US012770056B2

(12) United States Patent
Bhargava et al.

(10) Patent No.: US 12,770,056 B2
(45) Date of Patent: Oct. 20, 2026

(54) SYSTEMS AND METHODS FOR ADAPTATIVE TRAINING OF MACHINE LEARNING MODELS

(71) Applicant: PRENOSIS, INC., Chicago, IL (US)

(72) Inventors: Akhil Bhargava, Chicago, IL (US); Ishan Taneja, Chicago, IL (US); Carlos G. Lopez-Espina, Chicago, IL (US); Bobby Reddy, Jr., Chicago, IL (US); Sihai Dave Zhao, Chicago, IL (US); Ruoqing Zhu, Chicago, IL (US)

(73) Assignee: PRENOSIS, INC., Chicago, IL (US)

( * ) Notice: Subject to any disclaimer, the term of this patent is extended or adjusted under 35 U.S.C. 154(b) by 831 days.

(21) Appl. No.: 18/029,636

(22) PCT Filed: Oct. 1, 2021

(86) PCT No.: PCT/US2021/053251
§ 371 (c)(1),
(2) Date: Mar. 30, 2023

(87) PCT Pub. No.: WO2022/072892
PCT Pub. Date: Apr. 7, 2022

(65) Prior Publication Data

US 2023/0368070 A1 Nov. 16, 2023

Related U.S. Application Data

(60) Provisional application No. 63/086,977, filed on Oct. 2, 2020.

(51) Int. Cl.
*G06N 20/00* (2019.01)
*G16H 10/60* (2018.01)

(52) U.S. Cl.
CPC ............ *G06N 20/00* (2019.01); *G16H 10/60* (2018.01)

(58) Field of Classification Search
None
See application file for complete search history.

(56) References Cited

U.S. PATENT DOCUMENTS

| | | | | |
|---|---|---|---|---|
| 11,210,144 | B2 * | 12/2021 | Goodsitt | G06F 9/541 |
| 2006/0200253 | A1 | 9/2006 | Hoffberg et al. | |

(Continued)

FOREIGN PATENT DOCUMENTS

| | | |
|---|---|---|
| CN | 110503187 | 11/2019 |
| CN | 110691548 | 1/2020 |

(Continued)

OTHER PUBLICATIONS

International Search Report and Written Opinion issued in corresponding PCT Application No. PCT/US2021/053251, mailed Dec. 28, 2021.

(Continued)

*Primary Examiner* — Haimei Jiang
(74) *Attorney, Agent, or Firm* — Haynes and Boone, LLP

(57) ABSTRACT

A system for adapting a machine learning model for a specific population. The system includes a processor and memory devices storing instructions that configure the memory devices to perform operations. The operations may include receive a local dataset comprising local records of patients associated with the healthcare facility, perform a clustering function, and retrieving a template dataset comprising template records organized in clusters with variable centroids. The operations may also include calculating a similarity metric between the local and template records, generating a synthetic dataset by combining template and local records, segregating the synthetic dataset into a training synthetic dataset and a testing synthetic dataset, and generating and/or validating a machine learning predictive (Continued)

model by tuning a template model according to the training synthetic dataset and/or generating a new predictive model.

20 Claims, 25 Drawing Sheets

(56) References Cited

U.S. PATENT DOCUMENTS

| | | | |
|---|---|---|---|
| 2008/0201280 A1 | 8/2008 | Martin et al. | |
| 2009/0287546 A1 | 11/2009 | Gillespie et al. | |
| 2011/0022414 A1 | 1/2011 | Ge et al. | |
| 2015/0363556 A1 | 12/2015 | Sheldon et al. | |
| 2016/0162779 A1 | 6/2016 | Marcus et al. | |
| 2016/0335550 A1 | 11/2016 | Achin et al. | |
| 2017/0357760 A1 | 12/2017 | Han et al. | |
| 2020/0104412 A1 | 4/2020 | Bart | |
| 2020/0211716 A1 | 7/2020 | Lefkofsky et al. | |
| 2022/0156177 A1* | 5/2022 | Levacher | G06F 11/3692 |
| 2022/0374605 A1* | 11/2022 | Sethi | G06F 1/3209 |

FOREIGN PATENT DOCUMENTS

| | | | |
|---|---|---|---|
| EP | 3591586 A1 * | 1/2020 | G06N 3/126 |
| EP | 3648016 | 5/2020 | |
| JP | 2002-336193 | 11/2002 | |
| JP | 2011-227838 | 11/2011 | |
| JP | 2014-178229 | 9/2014 | |
| WO | WO 2017049034 | 3/2017 | |
| WO | WO 2019/129884 | 7/2019 | |

OTHER PUBLICATIONS

Klejch et al., "Speaker adaptive training using model agnostic meta-learning", *IEEE Automatic Speech Recognition and Understanding Workshop* (*ASRU*), 2019.

Narayanan et al., "Improving robustness of deep neural network acoustic models via speech separation and joint adaptive training", *IEEE/ACM transactions on audio, speech, and language processing*, 23(1): pp. 92-101, 2014.

* cited by examiner

1200

1700

SYSTEMS AND METHODS FOR ADAPTATIVE TRAINING OF MACHINE LEARNING MODELS

CROSS-REFERENCE TO RELATED APPLICATIONS

This application is a national phase application under 35 U.S.C. § 371 of International Application No. PCT/US2021/053251, filed Oct. 1, 2021, which claims priority to and the benefit of Provisional Application No. 63/086,977, filed Oct. 2, 2020, which are hereby incorporated by reference in its entirety as if fully set forth below and for all applicable purposes.

TECHNICAL FIELD

The present disclosure generally relates to systems and methods for adaptative training of machine learning models and, more particularly, to systems and methods for generating machine learning models customized for healthcare facilities using synthetic datasets that expand training and testing datasets.

BACKGROUND

Machine Learning (ML) is the field of study that explores the development of computer algorithms capable of learning from data and leverage learned patterns to make predictions. ML models are generated based on data that is used to train the ML algorithms for predictive operations. In ML, the quality and quantity of the training datasets is crucial for generating successful models because the training datasets define functions and calibrations that allow the models to perform predictions. ML models that are generated with insufficient or inadequate training datasets can perform poorly, while ML models generated with large and carefully curated training datasets can have good predictability and performance.

The amount and quality of training data required for successfully training a ML model depends on multiple factors, such as the number of classes that get categorized, the complexity of the prediction, whether the system may use pre-trained parameters, and uniformity between samples of the training data set. Additionally, the scope and quality of training datasets depends on the target classifier, the number of features considered, and the target application. But frequently, to achieve an ML model with high accuracy and good predictability, the training datasets need to be of a large size and high quality. Further, the training datasets need to include variety, subtlety, and nuance to prevent issues like overfitting and allow the generation of viable machine learning models for practical uses.

Creating large and high-quality training datasets for training ML models can be time consuming and expensive. Generating or compiling effective training datasets presents technical problems related to avoiding biases, labeling data, and/or formatting datasets. For example, before training datasets can be used to generate ML models, they must be curated to avoid biases or errors that corrupt ML model performance. Further, training datasets need to be formatted carefully so they can be fed to the ML algorithms. Moreover, creating datasets can be challenging because data labeling can require specialized tools that accurately label records. Indeed, the cost of generating and compiling training datasets can be particularly high in certain fields in which collecting samples require specialized equipment or personal. In those fields, training datasets create significant roadblocks that prevent developing successful ML models.

The disclosed systems and methods address one or more of the problems set forth above and/or other problems in the prior art.

SUMMARY

One aspect of the present disclosure is directed to a system for adapting a machine learning model for a specific population. The system may include one or more processors and one or more memory devices storing instructions that configure the one or more processors to perform operations. The operations may include receiving (from a healthcare facility) a local dataset comprising local records of patients associated with the healthcare facility and retrieving (from a database) a template dataset comprising template records, the template records being organized in clusters comprising variable centroids. The operations may also include calculating a similarity metric (e.g. clustering) between the local records and the template records by comparing demographics and the variable centroids, generating a synthetic dataset by combining at least a portion of the template records and at least a portion of the local records (the portion of the template records being selected based on a threshold similarity), and segregating the synthetic dataset into a training synthetic dataset and a testing synthetic dataset. The operations may further include generating a machine learning predictive model by performing at least one of tuning a template model according to the training synthetic dataset or generating a new predictive model and validating the tuned template model or the new predictive model employing the testing synthetic dataset.

Another aspect of the present disclosure is directed to a computer implemented method for adapting a machine learning model to a specific population. The method may include receiving (from a healthcare facility) a local dataset comprising local records of patients associated with the healthcare facility and retrieving (from a database) a template dataset comprising template records, the template records being organized in clusters comprising variable centroids. The method may also include calculating a similarity metric (e.g. clustering) between the local records and the template records by comparing demographics and the variable centroids, generating a synthetic dataset by combining at least a portion of the template records and at least a portion of the local records (the portion of the template records being selected based on a threshold similarity), and segregating the synthetic dataset into a training synthetic dataset and a testing synthetic dataset. The method may further include generating a machine learning predictive model by performing at least one of tuning a template model according to the training synthetic dataset or generating a new predictive model and validating the tuned template model or the new predictive model employing the testing synthetic dataset.

Yet another aspect of the present disclosure is directed to a computer-implemented apparatus including at least one processor and at least one memory device that configures the at least one processor to receive (from a healthcare facility) a local dataset comprising local records of patients associated with the healthcare facility and retrieve (from a database) a template dataset comprising template records, the template records being organized in clusters comprising variable centroids. The at least one processor may also be configured to calculate a similarity metric (e.g. clustering) between the local records and the template records by comparing demographics and the variable centroids, generate a synthetic dataset by combining at least a portion of the template records and at least a portion of the local records, the portion of the template records being selected based on a threshold similarity, segregate the synthetic dataset into a training synthetic dataset and a testing synthetic dataset, and generate a machine learning predictive model by (1) performing at least one of tuning a template model according to the training synthetic dataset or generating a new predictive model and (2) validating the tuned template model or the new predictive model employing the testing synthetic dataset.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

In the figures, elements and steps denoted by the same or similar reference numerals are associated with the same or similar elements and steps, unless indicated otherwise.

DETAILED DESCRIPTION

Figure 1:
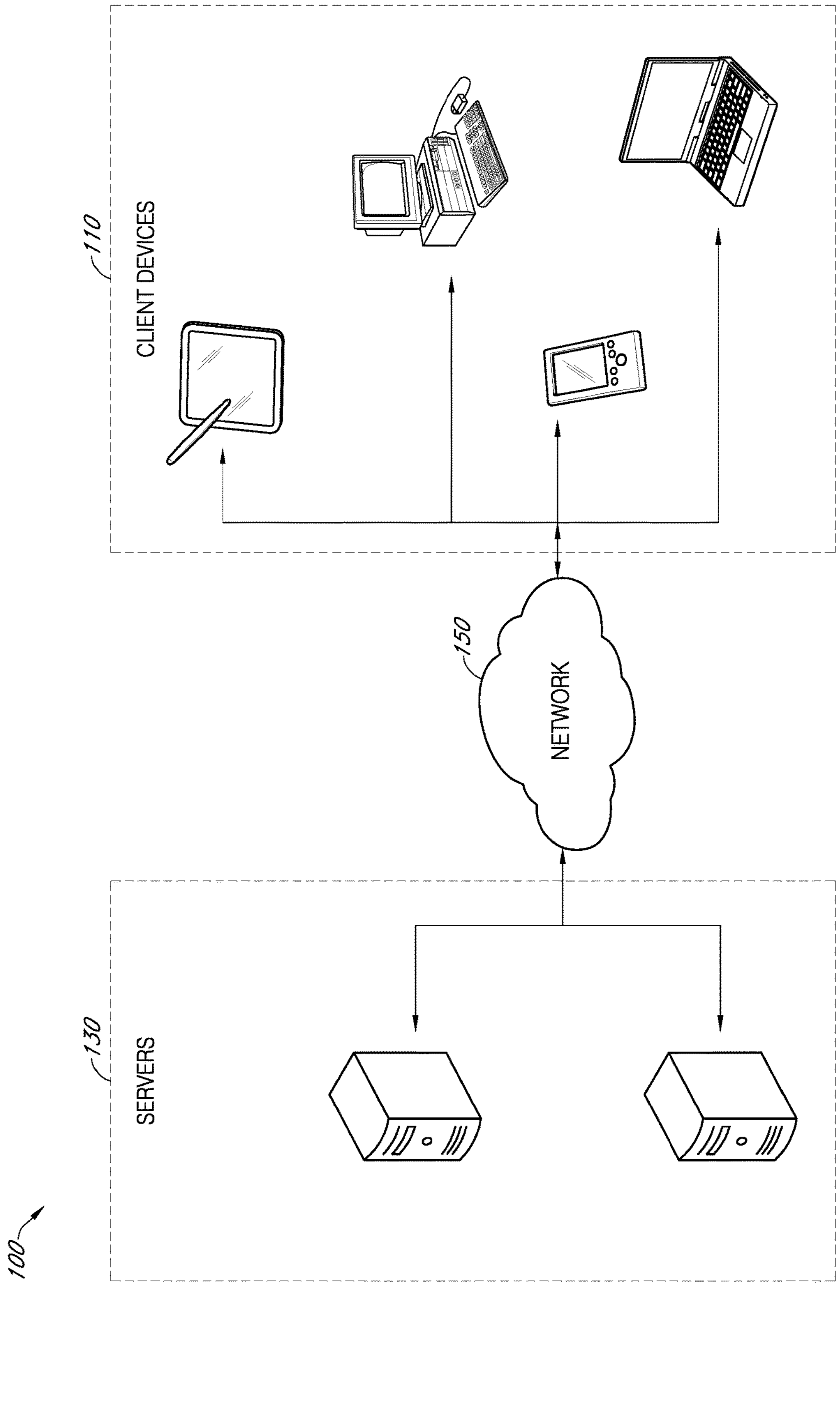
FIG. 1 illustrates an exemplary architecture suitable for implementing machine learning methods, in accordance with disclosed embodiments.

In the following detailed description, numerous specific details are set forth to provide a full understanding of the present disclosure. It will be apparent, however, to one ordinarily skilled in the art, that the embodiments of the present disclosure may be practiced without some of these specific details. In other instances, well-known structures and techniques have not been shown in detail so as not to obscure the disclosure.

Developers of ML, artificial intelligence (AI), and neural network (NN) models often face the challenge of compiling meaningful training datasets that allow them to train accurate models. Training datasets have heavy requirements, of quantity and quality, and ought to be tailored for the complexity of the targeted predictive task. Compiling training datasets can be particularly challenging in healthcare environments where data collection requires careful operation of specialized equipment and/or consideration of multiple factors and variables. In healthcare environments, generating training datasets is time-consuming and expensive, requires employing security measures, and must consider the unique needs of the healthcare industry— such as regulatory compliance.

Systems using ML/AI/NN algorithms desirably have complete sets of input data available before the training of the algorithms. However, in healthcare environments models may need to be generated for time-sensitive applications in which it is not possible to wait for the collection and processing of a complete and curated training datasets. The availability of training data creates one of the main bottlenecks for the development of usable ML/AI/NN models. This problem is exacerbated when models want to be tailored or customized for specific populations of patients to enhance predictability. Examples of such specific populations of patients include those patients that may exhibit a subset of a phenotype out of all possible phenotypes that exist. For instance, the models may be tailored for a patient population that may have more viral sepsis (e.g., in contrast to the patient population that may have more bacterial sepsis). Furthermore, a concept known as data-drift can occur where input features and/or the predictive label can undergo a shift in measurement or incidence rates. In such situations, it is not feasible to wait for complete training datasets for the targeted population. Such complexity, results in a computational problem that requires specific methods to, for example, quickly label and/or normalize records before they can be used in training operations.

Embodiments as disclosed herein provide a solution to the above problems in the form of a system that trains ML/AI/NN models using synthetic training and testing datasets. Various embodiments of the present disclosure include methods and systems for adaptative training of ML models using synthetic datasets that allow training high quality ML models without complete training datasets. The synthetic datasets leverage prior collected records, even if from a different population, to expand or improve the quality of training datasets available for a customized model focused on a target population. For example, when data from a healthcare facility is insufficient to train a robust ML model, disclosed systems and methods may allow the development of a synthetic dataset with enough records, variations, and quality to train a new customized model. Alternatively, or additionally, the disclosed systems and methods may allow the generation of synthetic records by adding variations to recorded healthcare information. These variations may be selected based on template models or statistical analysis. For example, the disclosed systems and methods may allow use of an expanded training set of biomarker records to train a predictive algorithm, such as a NN, by adding new records with statistically significant variations that have been observed in template records. Further, the expanded training set may be developed by applying mathematical transformation functions records of the healthcare facility to generate synthetic records. These transformations can include affine transformations (for example, shifting, mirroring, or filtering transformations) that alter the biomarker composition of a patient record. The application of mathematical transformation functions to generate synthetic records (e.g., by altering biomarker composition of patient records) can be an example of normalization of datasets such as the biomarker records to prepare for machine learning. Details related to normalization of datasets for machine learning can be found in Applicant's own International Application (PCT) Serial No.: PCT/US21/44943, filed Aug. 6, 2021, titled "Systems and Methods for Normalization of Machine Learning Datasets," incorporated by reference herein in its entirety. The ML models may then be trained with this expanded synthetic training set using stochastic learning with backpropagation or other ML algorithms that uses the gradient of a mathematical loss function to adjust the weights of the network.

The disclosed systems and methods may also improve the technical field of healthcare ML model generation by addressing technical problems that arise when classifying patients according to healthcare records. For example, the disclosed systems and methods allow for the generation of ML models that can predict healthcare outcomes with improved statistical measures such as but not limited to improved sensitivity, improved specificity, improved positive predictive value (PPV), improved negative predictive value (NPV), etc. For example, various embodiments of the disclosed systems and methods may minimize false positives by performing an iterative training and validation of algorithms using multiple versions of the synthetic data. In such embodiments, disclosed systems may generate multiple ML models with different training datasets that are then compared against each other. The combination of training models with synthetic datasets and comparing the models with model evaluation, using objective metrics like key performance indicators (KPIs) such as length of stay, readmission, and mortality, provides a robust process for generation of models that can predict healthcare outcomes while limiting the number of false positives.

Moreover, disclosed embodiments may improve computer functionality by minimizing computational expense of generating new ML models. Various embodiments of the disclosed systems and methods may facilitate the selection of records in a training dataset based on similarity analysis between two datasets. In such embodiments, disclosed systems may filter records that are not necessary for training an ML model to reduce occupation of computer resources during the generation of models. Disclosed systems and methods allow the identification of missing features of behaviors to specifically add synthetic records to a training dataset without including redundant or unnecessary records. The disclosed systems and methods improve computer functionality by constraining the number of records that are created in synthetic datasets to minimize computer resources employed during training of ML models.

Reference will now be made to the accompanying drawings, which describe exemplary embodiments of the present disclosure.

FIG. 1 illustrates an example architecture 100 for implementing machine learning methods, in accordance with disclosed embodiments. Architecture 100 includes servers 130 and client devices 110 connected over a network 150. One of the many servers 130 is configured to host a memory including instructions which, when executed by a processor, cause the server 130 to perform at least some of the steps in methods as disclosed herein. At least one of servers 130 may include, or have access to, a database including clinical data for multiple patients.

Servers 130 may include any device having an appropriate processor, memory, and communications capability for hosting the collection of images and a trigger logic engine. The trigger logic engine may be accessible by various client devices 110 over network 150. Client devices 110 can be, for example, desktop computers, mobile computers, tablet computers (e.g., including e-book readers), mobile devices (e.g., a smartphone or PDA), or any other devices having appropriate processor, memory, and communications capabilities for accessing the trigger logic engine on one of servers 130. In accordance to various embodiments, client devices 110 may be used by healthcare personnel such as physicians, nurses or paramedics, accessing the trigger logic engine on one of servers 130 in a real-time emergency situation (e.g., in a hospital, clinic, ambulance, or any other public or residential environment). In various embodiments, one or more users of client devices 110 (e.g., nurses, paramedics, physicians, and other healthcare personnel) may provide clinical data to the trigger logic engine in one or more server 130, via network 150.

In yet other embodiments, one or more client devices 110 may provide the clinical data to server 130 automatically. For example, in various embodiments, client device 110 may be a blood testing unit in a clinic, configured to provide patient results to server 130 automatically, through a network connection. Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like.

Figure 2:
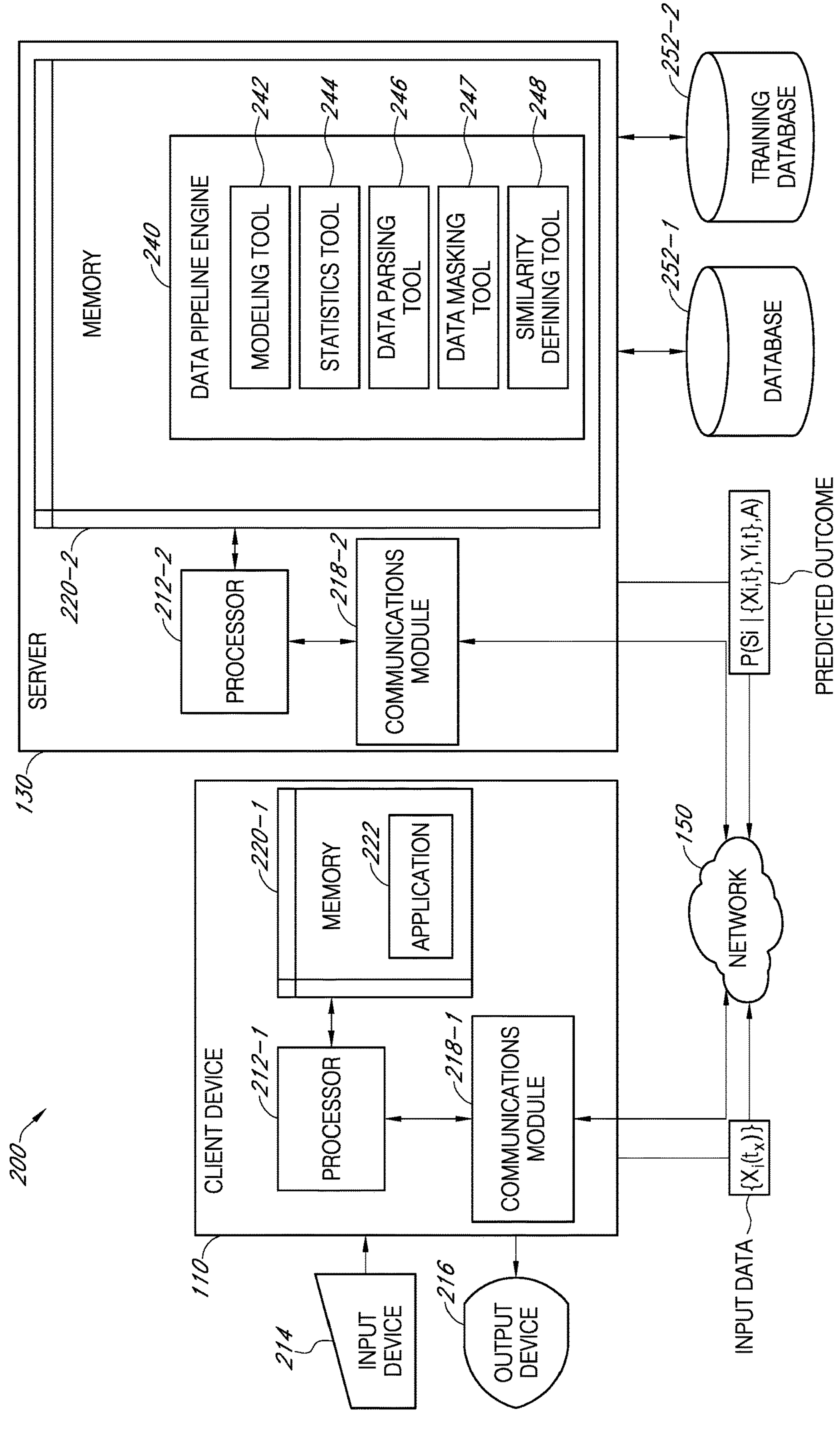
FIG. 2 illustrates a block diagram of an exemplary server and client in a machine learning system, according to disclosed embodiments.

FIG. 2 is a block diagram 200 illustrating an example server 130 and client device 110 in the architecture 100 of FIG. 1, according to various aspects of the disclosure. Client device 110 and server 130 are communicatively coupled over network 150 via respective communications modules 218-1 and 218-2 (hereinafter, collectively referred to as "communications modules 218"). Communications modules 218 are configured to interface with network 150 to send and receive information, such as data, requests, responses, and commands to other devices on the network. Communications modules 218 can be, for example, modems or Ethernet cards. Client device 110 and server 130 may include a memory 220-1 and 220-2 (hereinafter, collectively referred to as "memories 220"), and a processor 212-1 and 212-2 (hereinafter, collectively referred to as "processors 212"), respectively. Memories 220 may store instructions which, when executed by processors 212, cause either one of client device 110 or server 130 to perform one or more steps in methods as disclosed herein. Accordingly, processors 212 may be configured to execute instructions, such as instructions physically coded into processors 212, instructions received from software in memories 220, or a combination of both.

In accordance with various embodiments, server 130 may include, or be communicatively coupled to, a database 252-1 and a training database 252-2 (hereinafter, collectively referred to as "databases 252"). In one or more implementations, databases 252 may store clinical data for multiple patients. In accordance with various embodiments, training database 252-2 may be the same as database 252-1, or may be included therein. The clinical data in databases 252 may include metrology information such as non-identifying patient characteristics; vital signs; blood measurements such as complete blood count (CBC), comprehensive metabolic panel (CMP), and blood gas (e.g., Oxygen, $CO2$, and the like); immunologic information; biomarkers; culture; and the like. The non-identifying patient characteristics may include age, gender, and general medical history, such as a chronic condition (e.g., diabetes, allergies, and the like). In various embodiments, the clinical data may also include actions taken by healthcare personnel in response to metrology information, such as therapeutic measures, medication administration events, dosages, and the like. In various embodiments, the clinical data may also include events and outcomes occurring in the patient's history (e.g., sepsis, stroke, cardiac arrest, shock, and the like). Although databases 252 are illustrated as separated from server 130, in various aspects, databases 252 and data pipeline engine 240 can be hosted in the same server 130, and be accessible by any other server or client device in network 150.

Memory 220-2 in server 130 may include a data pipeline engine 240 for evaluating and processing input data from a healthcare facility to generate training datasets. Data pipeline engine 240 may include a modeling tool 242, a statistics tool 244, a data parsing tool 246, a data masking tool 247, and a similarity defining tool 248. Modeling tool 242 may include instructions and commands to collect relevant clinical data and evaluate a probable outcome. Modeling tool 242 may include commands and instructions from a linear model, an ensemble machine learning model such as random forest or a gradient boosting machine, and a neural network (NN), such as a deep neural network (DNN), a convolutional neural network (CNN), and the like. According to various embodiments, modeling tool 242 may include a machine learning algorithm, an artificial intelligence algorithm, or any combination thereof.

Statistics tool 244 evaluates prior data collected by trigger logic engine 240, stored in databases 252, or provided by modeling tool 242. In various embodiments, statistics tool 244 may also define normalization functions or methods based on data requirements provided by modeling tool 242. Imputation tool 246 may provide modeling tool 242 with data inputs otherwise missing from a metrology information collected by trigger logic engine 240. Data parsing tool 246 may handle real-time data feeds and connect to external systems. Data parsing tool 246 may automatically label and characterize data optimized for efficiency and using group messages to reduce the overhead of the network. Data masking tool 247 may perform operations to create structurally similar but inauthentic version of healthcare records that, for example, remove personal identifiable information. Data masking tool 247 may be configured to protect the actual data while having a functional substitute for ML training. Similarity defining tool 248, may perform operations for evaluating similarities between two datasets. For example, similarity defining tool 248 may employ comparative operations between clusters or vectors in two datasets like norms such as L2 norm, L1 norm, or other hybrid norms, or distance metrics such as Euclidean Distance, Manhattan Distance, Minkowski Distance or other distance metrics. Alternatively, or additionally, similarity defining tool 248 may be configured to extract feature differences between datasets and/or identify similar and dissimilar records.

Client device 110 may access trigger logic engine 240 through an application 222 or a web browser installed in client device 110. Processor 212-1 may control the execution of application 222 in client device 110. In accordance with various embodiments, application 222 may include a user interface displayed for the user in an output device 216 of client device 110 (e.g., a graphical user interface, GUI). A user of client device 110 may use an input device 214 to enter input data as metrology information or to submit a query to trigger logic engine 240 via the user interface of application 222. In accordance with various embodiments, an input data, $\{Xi(tx)\}$, may be a $1\times n$ vector where $Xij$ indicates, for a given patient, i, a data entry j ($0\leq j\leq n$), indicative of any one of multiple clinical data values (or stock prices) that may or may not be available, and tx indicates a time when the data entry was collected. Client device 110 may receive, in response to input data $\{Xi(tx)\}$, a predicted outcome $P(Si|\{Xi,t\}, Yi,t\}, A)$, from server 130. In accordance to various embodiments, predicted outcome $P(Si|\{Xi,t\}, Yi,t\}, A)$, may be determined based not only on input data, $\{Xi(tx)\}$, but also on an imputed data, $\{Yi(tx)\}$.

Accordingly, imputed data {Yi(tx)} may be provided by imputation tool 246 in response to missing data from the set {Xi(tx)}. In various embodiments, predicted outcome P(Si|{Xi,t}, Yi,t}, A) may be sent to client devices in with an associated ranking of importance to enable validations and/or user review. Input device 214 may include a stylus, a mouse, a keyboard, a touch screen, a microphone, or any combination thereof. Output device 216 may also include a display, a headset, a speaker, an alarm or a siren, or any combination thereof.

Figure 3:
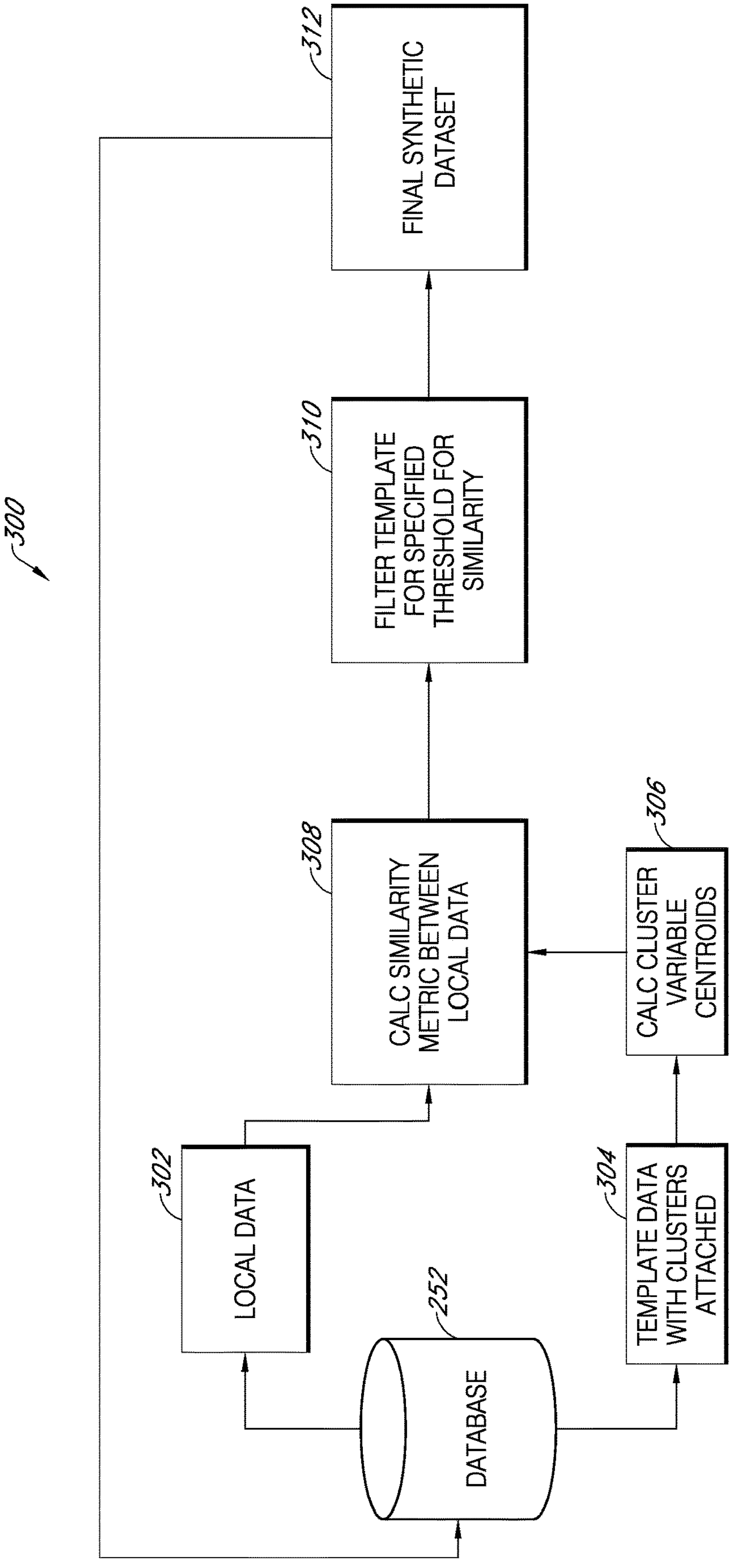
FIG. 3 illustrates an exemplary workflow for generating of synthetic datasets, according to disclosed embodiments.

FIG. 3 illustrates an exemplary workflow 300 for generating of synthetic datasets, according to disclosed embodiments. In various embodiments, one or more client devices and servers as disclosed herein may perform workflow 300. More specifically, a processing engine including data pipeline engine 240 with a modeling tool and a statistics tool may be used for workflow 300.

In workflow 300, database 252 may provide local data in operation 302. The local data may include healthcare records or patients of a target healthcare facility and may retrieved as a CSV file or similar data record files. Database 252 may also provide template data with clusters attached in operation 304. The template data may include data from sample healthcare facilities or historic patient information.

In operation 306, clusters with variable centroids may be calculated and based on the calculated clusters and centroids, similarity metrics between local data and template data may get calculated in operation 308. For example, similarity defining tool 248 may calculate similarity metrics between local and template records. As further described in connection with FIG. 18, the similarity definitions may be based on distances between clustered groups. Based on the similarity determinations, records may be filtered in operation 310. For example, data pipeline engine 240 may filter template records based on a specified similarity threshold.

In operation 312, a final synthetic data set may be generated. For example, data pipeline engine 240 may generate a synthetic data set that includes local records of the target healthcare center (i.e., the healthcare center for which the new model is being generated) and template records that are not filtered in operation 310. As shown in FIG. 3, in various embodiments the final synthetic dataset may be stored in database 252.

Figure 4:
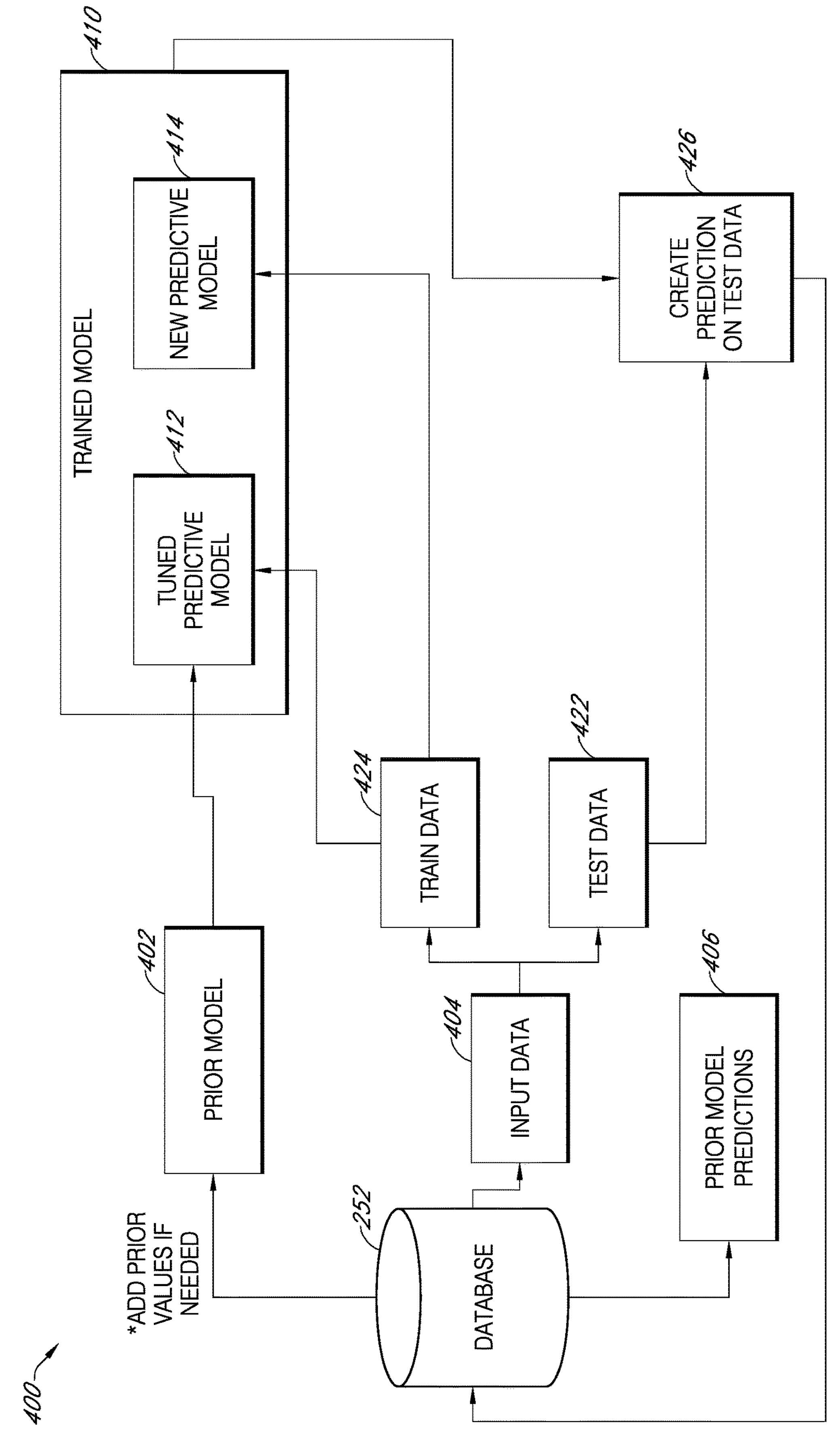
FIG. 4 illustrates an exemplary workflow of for training models tailored for local records based on prior models, in accordance with various embodiments.

FIG. 4 illustrates an exemplary workflow 400 of for training models tailored for local records based on prior models, in accordance with various embodiments. In various embodiments, one or more client devices and servers as disclosed herein may perform workflow 400. More specifically, a processing engine, including data pipeline engine 240, may be used for workflow 400.

In workflow 300, database 252 may provide prior model data in operation 302, input data in operation 404, and prior model predictions in operation 406. The input data may be segregated in train data, in operation 424, and test data, in operation 422. The test data may be used to create predictions on test data in operation 426. While the train data may be used to train a ML model in operation 410. As shown in FIG. 4, the model may be trained by tuning a predictive model using the training data or by generating a new predictive model based on the training data.

Figure 5A:
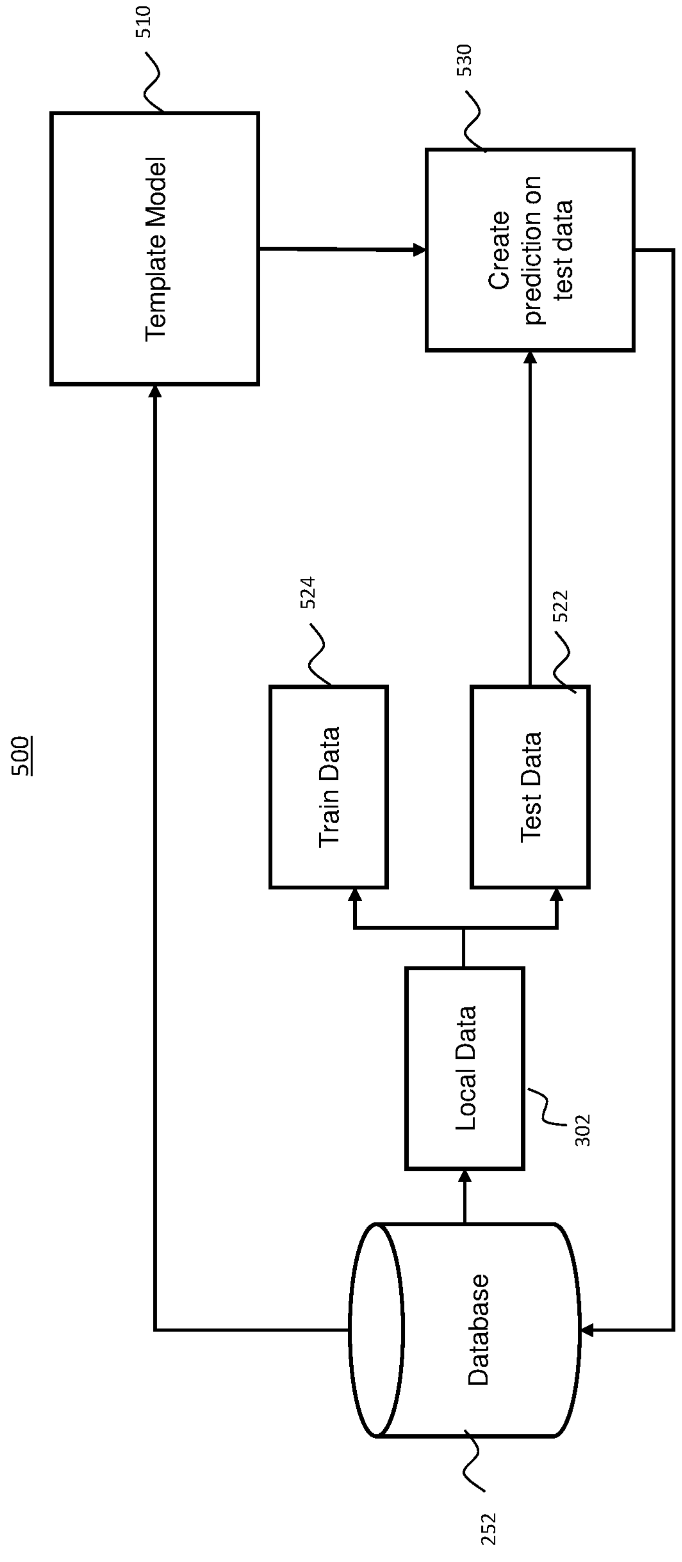
FIG. 5A illustrates an exemplary workflow of a model generation process based on template models, in accordance with various embodiments.

FIG. 5A illustrates an exemplary workflow 500 of a model generation process based on template models, in accordance with various embodiments. In various embodiments, one or more client devices and servers as disclosed herein may perform workflow 500. More specifically, a processing engine, including data pipeline engine 240, may be used for workflow 500.

In workflow 500, like in workflow 300, database 252 may provide local data in operation 302, the local data may include patient records of the target healthcare facility. However, in addition to providing local data, database 252 may provide a template model in operation 510. The template model may include ML models that have been generated for other healthcare facilities and/or public ML models or datasets.

The local data may be segregated in train data, in operation 524, and in test data, in operation 522. The test data and template model may be both used to create a predictive data test in operation 530. For example, data pipeline engine 240 may generate predictive test data by applying the test data of operation 522 with template models retrieved from database 252 in operation 510.

Figure 5B:
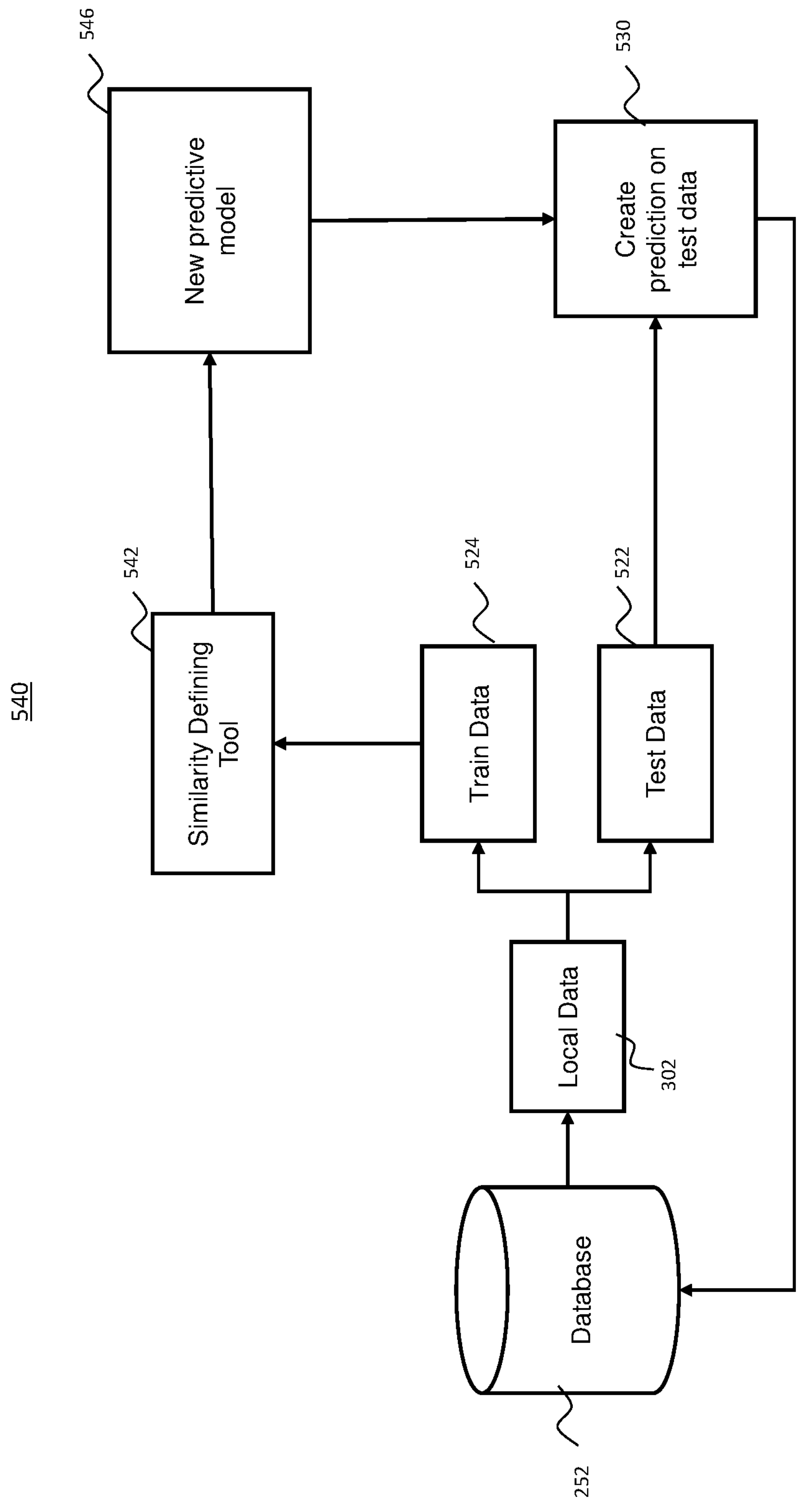
FIG. 5B illustrates an exemplary workflow of a model generation process based on similarity results, in accordance with various embodiments.

FIG. 5B illustrates an exemplary workflow 540 of a model generation process based on similarity results, in accordance with various embodiments. In various embodiments, one or more client devices and servers as disclosed herein may perform workflow 540. More specifically, a processing engine, including data pipeline engine 240, may be used for workflow 540.

Similar to workflow 500, in workflow 540 database 252 may provide local data in operation 302, which may be segregated in train data and test data in operations 524 and 522 respectively. However, unlike workflow 500, in workflow 540 a new predictive model may be generated in operation 546 through a similarity definition tool, such as similarity defining tool 248, in operation 542. The new predictive model and the test data may be used to create a prediction on test data in operation 530.

Figure 5C:
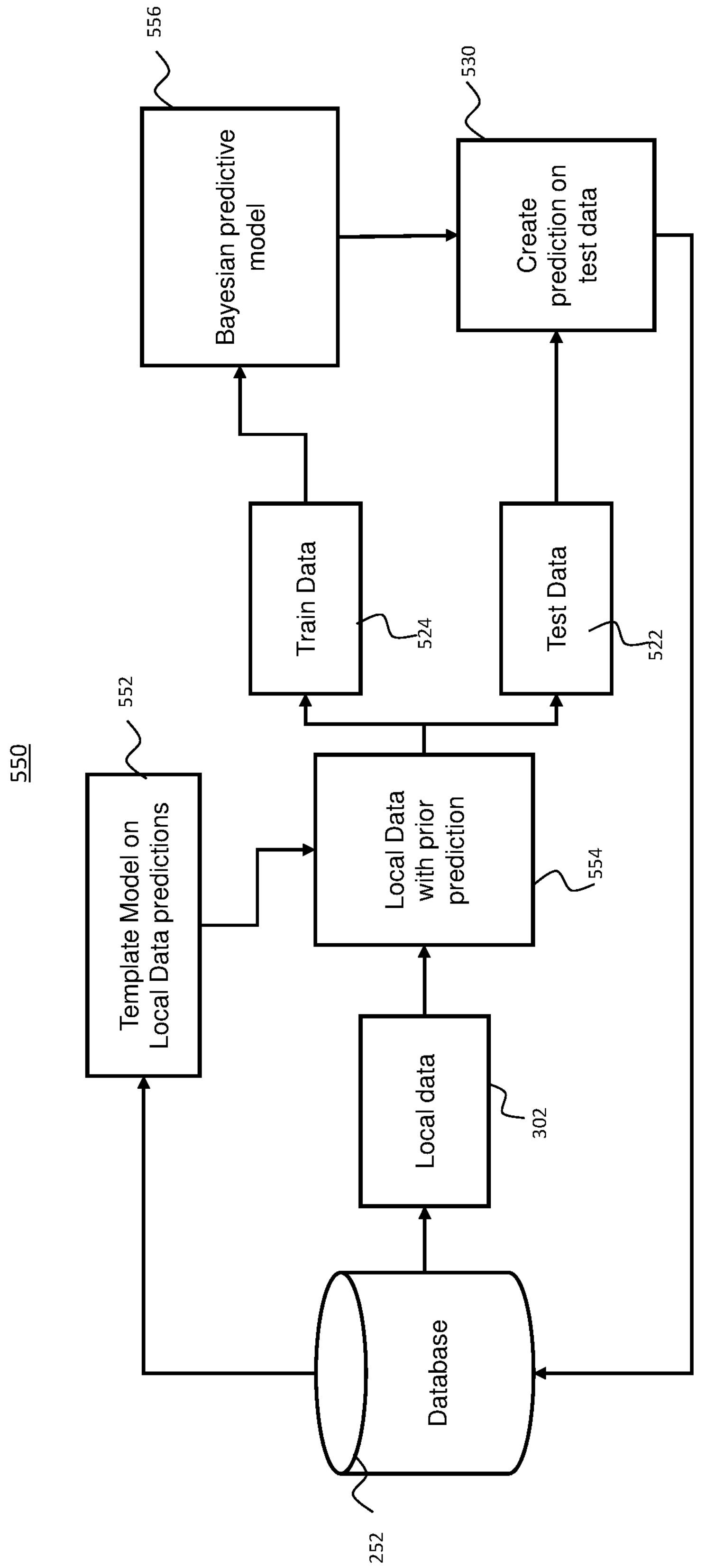
FIG. 5C illustrates an exemplary workflow of a model generation process based on local data predictions, in accordance with various embodiments.

FIG. 5C illustrates an exemplary workflow 550 of a model generation process based on local data predictions, in accordance with various embodiments. In various embodiments, one or more client devices and servers as disclosed herein may perform workflow 550. More specifically, a processing engine, including data pipeline engine 240, may be used for workflow 550.

Similar to workflow 540, in workflow 550 database 252 may provide local data in operation 302. However, unlike workflow 540, the local data 302 does not get segregated in training and test data. Rather, the local data is filtered and processed through a template model to generate local data predictions in operation 552 which can be used as a prior prediction in operation 554. In such embodiments, the local data may be separated after it is added with a prior prediction from the template model. Further, as shown in FIG. 5C, the template model on local data predictions may be retrieved from database 552.

In workflow 550, the train data may be used to generate a Bayesian predictive model in operation 556, which in combination with the test data may be used to create prediction on test data in operation 530.

Figure 5D:
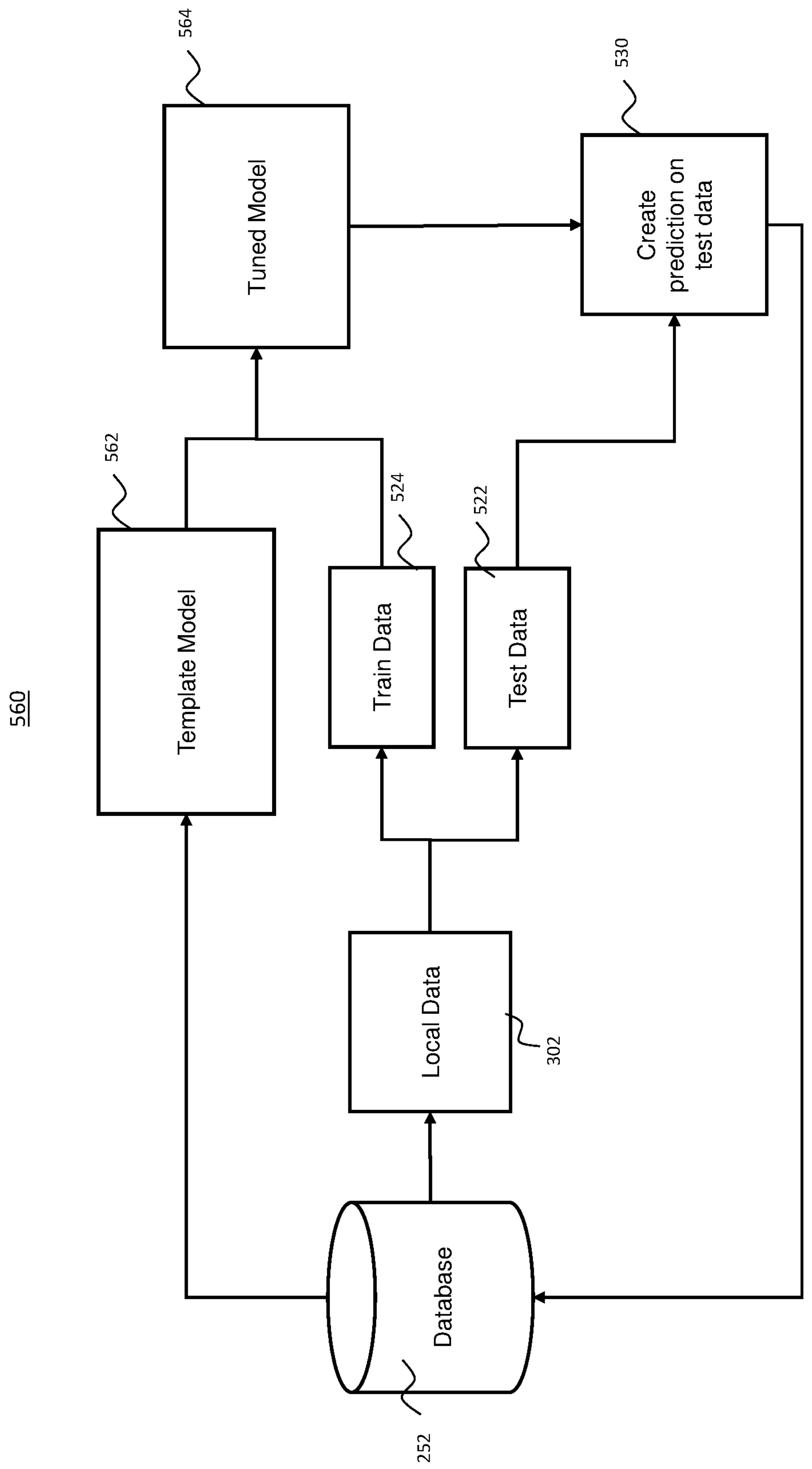
FIG. 5D illustrates an exemplary workflow of a model generation process based on tuning template models, in accordance with various embodiments.

FIG. 5D illustrates an exemplary workflow 560 of a model generation process based on tuning template models, in accordance with various embodiments. In various embodiments, one or more client devices and servers as disclosed herein may perform workflow 560. More specifically, a processing engine, including data pipeline engine 240, may be used for workflow 560.

Similar to workflow 500, in workflow 560 database 252 may provide local data in operation 302, which may be segregated in train data and test data in operations 524 and 522 respectively. In addition, in workflow 560 database 252 may provide a template model in operation 562.

The template model and the train data may be used to tune a model in operation 564. For example, the template model and the train data may be used to tune hyper parameters to tune a model in operation 564. The tuned model in combination with test data may be employed to create a prediction on test data in operation 530.

In some instances, the tuned template model may be validated by adjusting hyperparameters based on hospital key performance indicators (KPIs). Non-limiting examples of hospital KPIs include critical care outcome indicators, diagnostic indicators, etc. In some instances, critical care outcome indicators may include but are not limited to patient readmission rates (e.g., thirty-day readmission), mortality rates, intensive care unit (ICU) escalations, number of ventilator free days, number of ventilator days (i.e., number of days patients are on ventilators), number of vesopressor days (i.e., number of days patients are on vesopressors), length of stay at hospital, and/or the like. In some instances, diagnostic indicators may include but are not limited to PPV, NPV, sensitivity, specificity, true positive rates (TPRs), false positive rates (FPRs), and/or the like, of diagnoses performed at the hospital.

Figure 6:
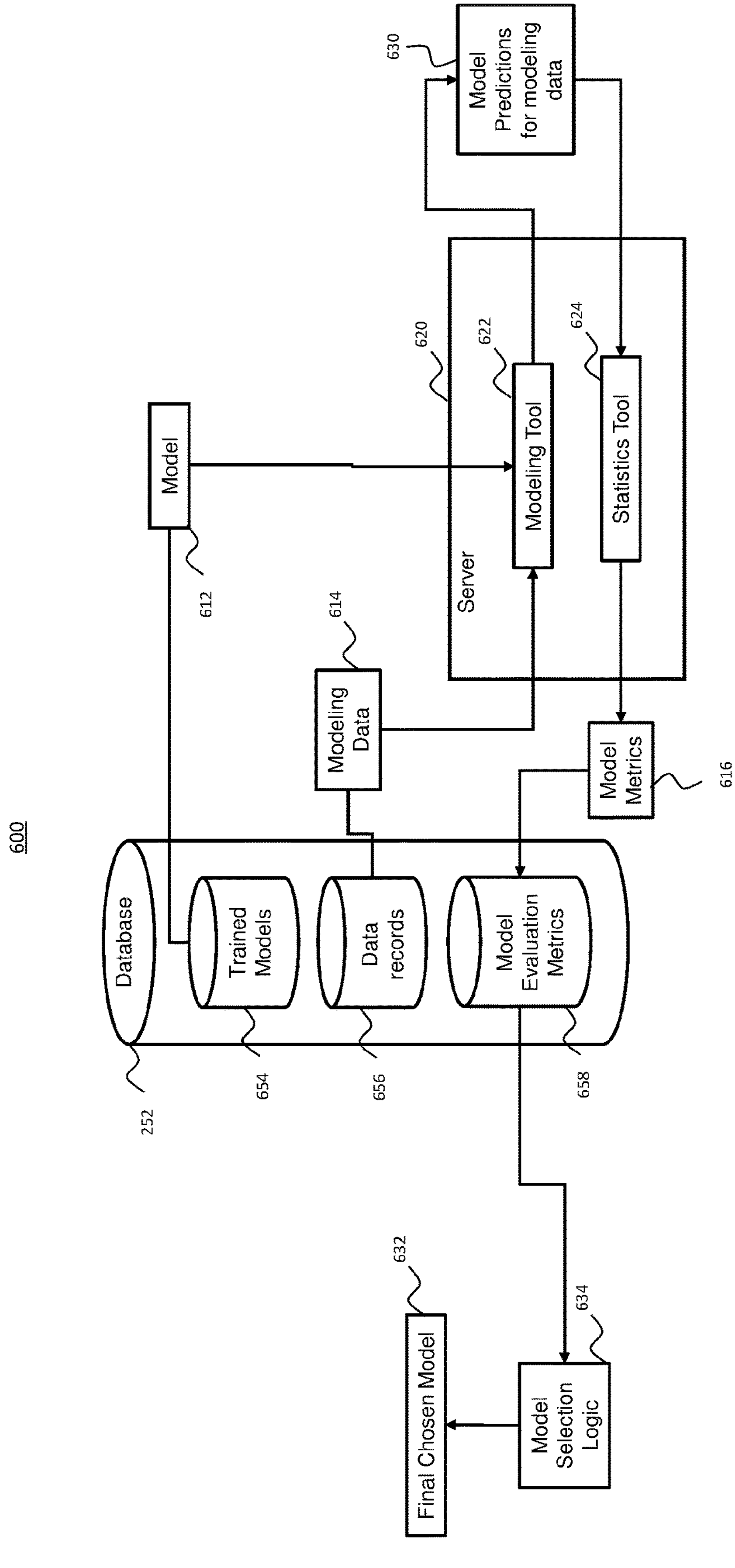
FIG. 6 illustrates an exemplary workflow for the evaluation and selection of trained models, in accordance with various embodiments.

FIG. 6 illustrates a workflow 600 for the evaluation and selection of trained models, in accordance with various embodiments. In various embodiments, as shown in FIG. 6, a combination of database 252 and one or more servers, as disclosed herein, may perform workflow 600.

Database 252 may include trained models 654, data records 656, and model evaluation metrics 658. Database 252 may provide models in operation 612 and modeling data in operation 614. The model and modeling data may be combined by a modeling tool (e.g., modeling tool 242) in operation 622. The modeling tool may generate model predictions for the modeling data. These predictions may be transmitted to a statistics tool (e.g., statistics tool 244) in operation 624.

The generated model prediction may also be evaluated under model metrics in operation 616 and the results of the evaluation may be stored in model evaluation metrics 658 of database 252.

In various embodiments, the model evaluation metrics may be used for the selection of a model using a model selection logic in operation 634. For example, when multiple models are generated using varying training datasets, a model selection logic may compare different models and identify the best performing model from the group, for example based on KPIs, and the final model is chosen in operation 632 of workflow 600.

Figure 7:
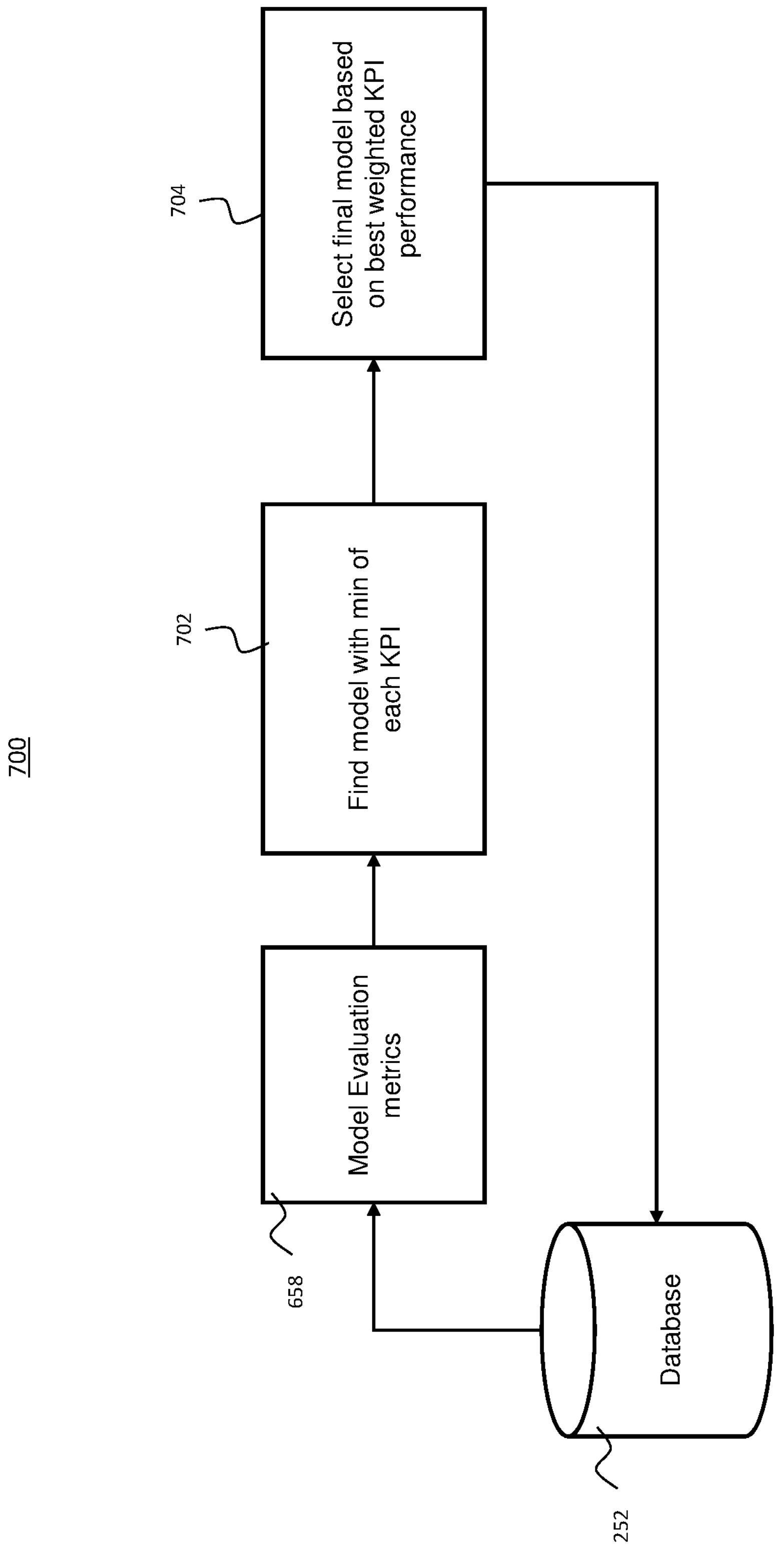
FIG. 7 illustrates an exemplary workflow for the selection of models based on key performance indicators (KPIs), in accordance with various embodiments.

FIG. 7 illustrates a workflow 700 for the selection of models based on key performance indicators (KPIs), in accordance with various embodiments. In various embodiments, one or more client devices and servers as disclosed herein may perform workflow 700. More specifically, a processing engine, including data pipeline engine 240, may be used for workflow 700.

Similar to workflow 600, in workflow 700 database 252 may provide model evaluation metrics in operation 658. Using model evaluation metrics, data pipeline engine 240 may identify a model with a minimum combination of KPIs in operation 702. Based the identified model, a final model may be selected 704 based on the best weighted KPI performance. For example, data pipeline engine 240 may select a final model based on a weighted KPI and model evaluation metric performance.

Figure 8:
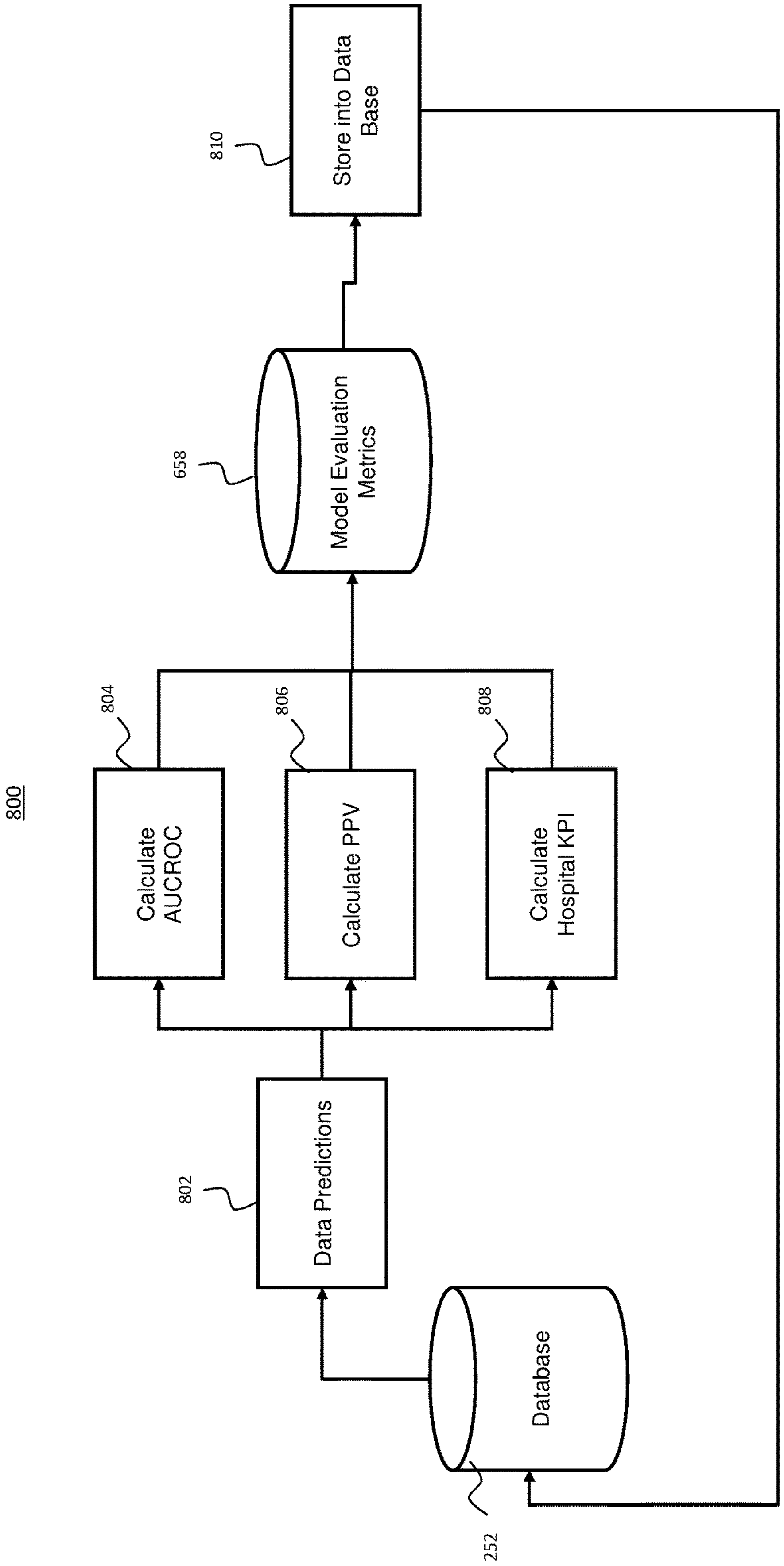
FIG. 8 illustrates an exemplary workflow for evaluation of adapted predictive models, in accordance with various embodiments.

FIG. 8 illustrates a workflow 800 for evaluation of adapted predictive models, in accordance with various embodiments. In various embodiments, one or more client devices and servers as disclosed herein may perform workflow 800. More specifically, a processing engine, including data pipeline engine 240, may be used for workflow 800.

In workflow 800, database 252 may provide data predictions in operation 802. The data predictions may be used to calculate objective metrics such as but not limited to sensitivity, specificity, PPV, NPV, area under the receiver operating characteristic (AUROC), PPV, hospital KPIs (e.g., patient readmission rate, patient length of stay at hospital, patient mortality, etc.), and/or the like. AUROC, PPV, hospital KPIs are calculated, using data predictions, in operations 804, 806, and 808. For example, data pipeline engine 240 may perform the calculations using the data protection. The AUCROC, PPV, and KPI calculations may be transferred to model evaluation metrics, in operation 658, and stored in database 252, in operation 810. In various embodiments, predictions can be used in the statistics tool to get an AUROC PPV and other traditional ML metrics. In such embodiments, the KPI's may be used by groupings created from the predictions to identify how separable these metrics via looking at the silhouette metric.

Figure 9:
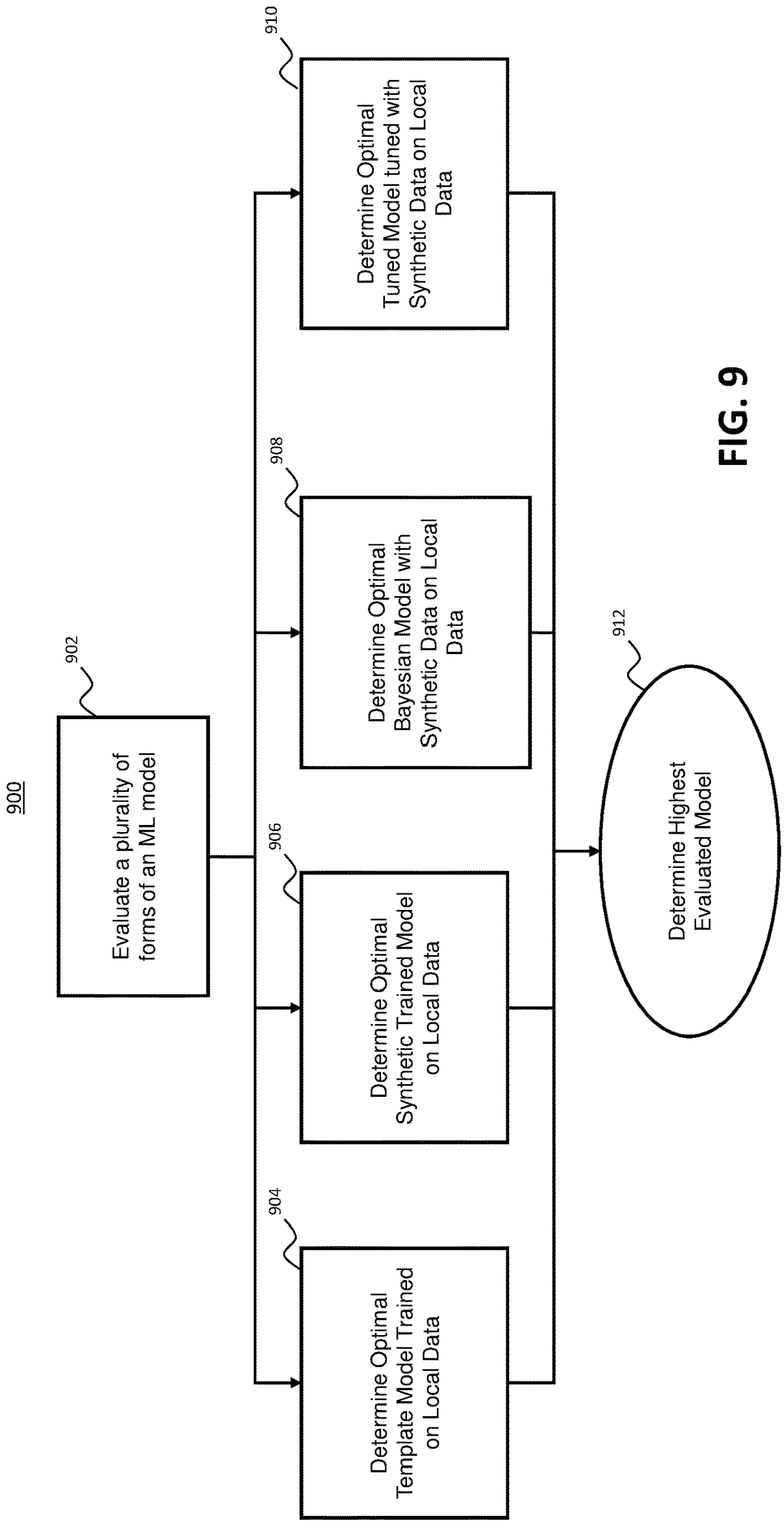
FIG. 9 illustrates a flow chart of a process for determining a higher performing model, in accordance with various embodiments.

FIG. 9 illustrates a flow chart of a method 900 for determining a higher performing model, in accordance with various embodiments. Method 900 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 900 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 900 may include retrieving, editing, and/or storing files in a database that is part of, or is communicably coupled to, the computer, using, inter-glia, a trigger logic engine (e.g., databases 252). Methods consistent with the present disclosure may include at least some, but not all, of the steps illustrated in method 900, performed in a different sequence. Furthermore, methods consistent with the present disclosure may include at least two or more steps as in method 900 performed overlapping in time, or almost simultaneously.

Step 902 includes evaluating a plurality of forms of an ML model. For example, the plurality of forms may be generated in steps 1502 through 1508 on FIG. 15.

Based on the step 902 model evaluation, multiple model optimizations may be performed in steps 904-910. The optimization may be performed in parallel, as shown in FIG. 9, but in various embodiments may be performed sequentially (not shown).

Step 904 includes determining an optimal template model data. For example, the optimal template model may be defined as using the optimal machine learning model trained upon only the template data.

Step 906 includes determining an optimal synthetic trained model. For example the optimal trained synthetic model may utilize a machine learning algorithm trained on the identified synthetic dataset from FIG. 10.

Step 908 includes determining an optimal Bayesian model. For example, the optimal Bayesian model may include the predictions of the local data generated from the optimal template model. These predictions may be used as an input a new model trained upon the local data.

Step 910 includes determining an optimal tuned model. For example, a previously trained model may be trained further upon the local data in order to produce a model tuned for the local data.

Figure 15:
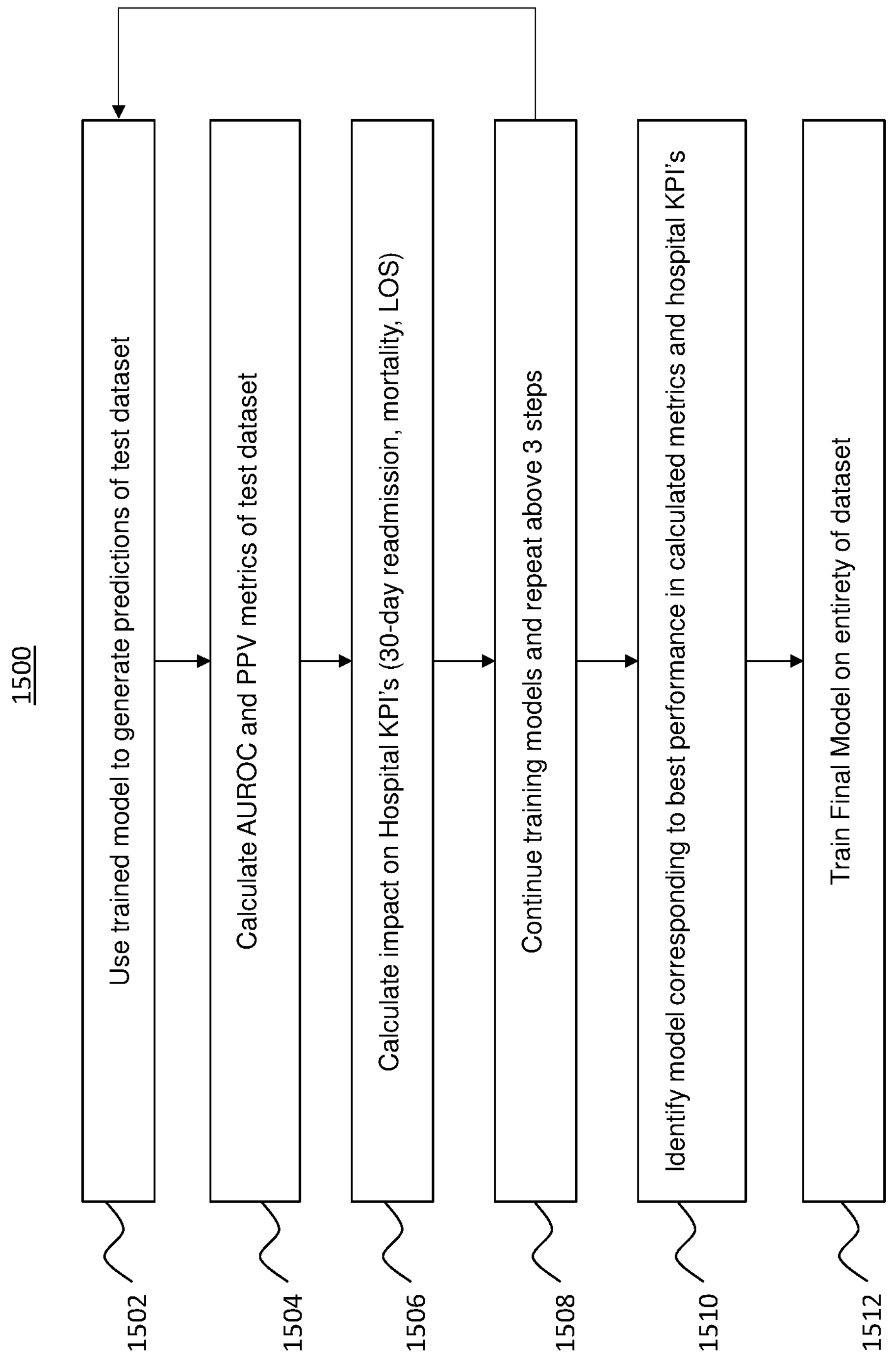
FIG. 15 illustrates a flow chart for training a machine learning model using training synthetic data, in accordance with various embodiments.

The optimized models of steps 904-910 may then be used to determine a highest evaluated model in step 912. For example, the optimal model may be found using a weighted calculate of KPI and model evaluation metrics of the test data as shown in FIG. 15.

Figure 10:
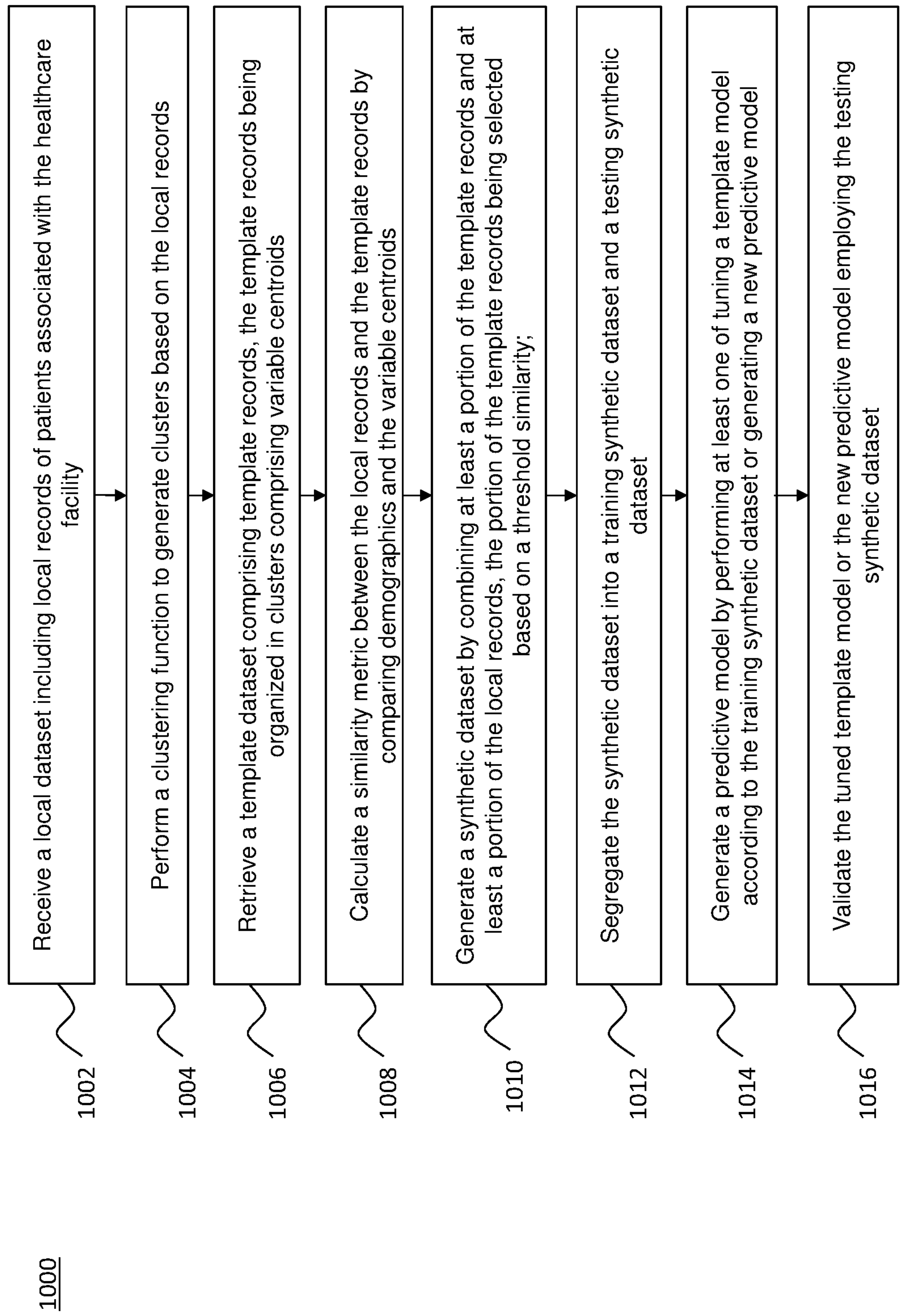
FIG. 10 illustrates a flow chart of a process for adapting a machine learning model for a specific population, in accordance with various embodiments.

FIG. 10 illustrates a flow chart of a method 1000 for adapting a machine learning model for a specific population, in accordance with various embodiments. In some instances, the specific population may be the population of patients that may exhibit a subset of a phenotype out of all possible phenotypes that exist. For instance, the specific population may be the patient population with more viral sepsis (e.g., in contrast to the patient population with more bacterial sepsis). Method 1000 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1000 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1000 may include retrieving, editing, and/or storing files in a database that is part of, or is communicably coupled to, the computer, using, inter-alia, a trigger logic engine (e.g., databases 252). Methods consistent with the present disclosure may include at least some, but not all, of the steps illustrated in method 1000, performed in a different sequence. Furthermore, methods consistent with the present disclosure may include at least two or more steps as in method 1000 performed overlapping in time, or almost simultaneously.

Step 1002 includes receiving a local dataset including local records of patients associated with the healthcare facility. The data may be received by pulling data from a hospital SQL database in 2-minute batches via an API. In various embodiments, in step 1002 the data is collected in approximately 2-minute batches. Further, step 1002 may include accessing the hospital's EMR data for a specific patient using a FHIR API.

Step 1004 includes performing a clustering function to generate clusters based on template records. In some instances, more than one clustering functions may be associated with the template records. For example, more than one clustering functions may be performed to generate the clusters based on the template records. Example clustering functions include a hierarchal method or a partitioning method.

Step 1006 includes retrieving a template dataset comprising template records, the template records being organized in clusters comprising variable centroids. In various embodiments, template and local records may have similar grouping centroids. In such embodiments, there is no constraint on adding more template data vs local data. Alternatively, or additionally, template records are stored within a database and in step 1006 the records are pulled to record mapping as stored or calculated in Step 1002.

Step 1008 includes calculating a similarity metric between the local records and the template records by comparing demographics and the variable centroids. For example, similarity from an individual local data record to template group may be calculated using a L1 Norm, or Minkowski Distance to determine the closest or most similar group.

Step 1010 includes generating a synthetic dataset by combining at least a portion of the template records and at least a portion of the local records, the portion of the template records being selected based on a threshold similarity from the template cluster centroids. Validation steps may include verifying presence of feature inputs in the template datasets which are required in the local dataset. A transformation step may be used to map the template data features and local data features if needed. Further validation steps may include comparing the local dataset to the new synthetic average and standard deviations for machine learning variables. For example, a process may include using univariate analysis to identify key features in machine learning or hospitalization outcomes deviate from the local dataset. Other processes may be used to detail a user specified outcome when the user specified minimum number of local data records are not present. The synthetic data may reside in training database 252-2.

Step 1012 includes segregating the synthetic dataset into a training synthetic dataset and a testing synthetic dataset. The data may have rules imposed that segregate the data into an 80% and 20% split, where no record ids are present in both splits. In various embodiments, the ratio between training synthetic dataset and the testing synthetic dataset is kept consistent across every model to compare models in the same test dataset.

Step 1014 includes generating a predictive model by performing at least one of tuning a template model according to the training synthetic dataset or generating a new predictive model. For example, the methods that may be followed are shown in FIG. 5. In various embodiments, the predictive model step 1014 may be configured to output risk scores for evaluating immune system deregulation. For example, the predictive model step 1014 may generate risk scores through an optimized thresholding process.

Step 1016 includes validating the tuned template model or the new predictive model employing the testing synthetic dataset. In various embodiments, validating the tuned model may include determining whether a baseline model (using the template model on the local data) is outperformed by any of the new models. In such embodiments, step 1016 may include performing a user defined number of revisions upon hyperparameters to streamline the process.

In various embodiments of method 1000, data streams may be processed in real time by the data parsing tool 246 and the local records may be deidentified by the data masking tool 247. In various embodiments, the database may comprise previously trained models, the template records, and model evaluation metrics.

In various embodiments, the generating the synthetic dataset comprises identifying missing clusters in the local dataset that are present in the template dataset. In various embodiments, the validating the tuned template model or the new predictive model comprises adjusting hyperparameters based on hospital key performance indicators (KPIs). In various embodiments, the clusters may be generated based on the template records by performing a clustering function including performing data normalization.

In various embodiments of method 1000, the generating the machine learning predictive model further comprises: generating a first tuned model by tailoring the template model using the local records as training data; generating a second tuned model by tailoring the template model using the training synthetic data; generating a first new model using the local records as training data; generating a second new model using the training synthetic dataset; and comparing the first tuned model, the second tuned model, the first new model, and the second new model to determine a highest evaluated model. In various embodiments, the comparing the first tuned model, the second tuned model, the first new model, and the second new model comprises selecting a final model based on weighted KPIs of the first tuned model, the second tuned model, the first new model, and the second new model. In some instances, one or more of the first tuned model, the second tuned model, the first new model, and the second new model may each include multiple versions, and as such the comparison of these models may include forming a subset of models from the multiple versions so that a final model may be selected based on weighted KPIs of the model versions in the subset of models.

In various embodiments, the generating the synthetic dataset comprises generating additional records based on the local records using median or mode imputation. In various embodiments, the generating the synthetic dataset comprises employing a Bayesian model to generate testing database on the local records. In various embodiments, the tuned template model and the new predictive model provide an initial treatment prediction for providing treatment to patients. For example, in some instances, the template model can be used to identify a treatment prediction for a patient, and the identified treatment prediction can be used as a base value of a new predictive model when the new predictive model is used to provide a treatment prediction for patients. Various embodiments of method 1000 further comprise assigning a treatment protocol for the providing treatment to second patients based on the initial treatment prediction, each treatment protocol being optimized based on the tuned template model and the new predictive model. Examples of treatments may include physician treatments such as but not limited to providing antibiotics, fluids, steroids, ventilators, anti-coagulation mediations, and/or the like.

In various embodiments, the local records and the template records comprise patient biomarker information retrieved from electronic health records of the healthcare facility. Various embodiments of method 1000 further comprise transmitting model results to the healthcare facility through a fast healthcare interoperability resources application programing interface. In various embodiments, the synthetic dataset is larger than the local dataset.

Various embodiments of method 1000 further comprise performing a clustering function to generate the clusters based on the template records. In various embodiments, the local records comprise biomarker records comprising a plurality of biomarker metadata fields. In various embodiments, the performing the clustering function comprises: generating a normalization vector comprising biomarker records including mismatching metadata fields that mismatch one or more of a plurality of template metadata fields in the template records; identifying adjustment functions for of the mismatching metadata fields; modifying data fields of biomarker records in the normalization vector by applying the adjustment functions to the data fields corresponding to the mismatching metadata fields; and generating a normalized data file comprising the modified biomarker records.

In various embodiments, the performing the at least one of tuning the template model according to the training synthetic dataset or generating the new predictive model comprises generating a model predicting probability of dysregulated host response caused by infection. In various embodiments, method 1000 can employ a statistics tool to generate model metrics; and storing the model metrics in the database.

Figure 11:
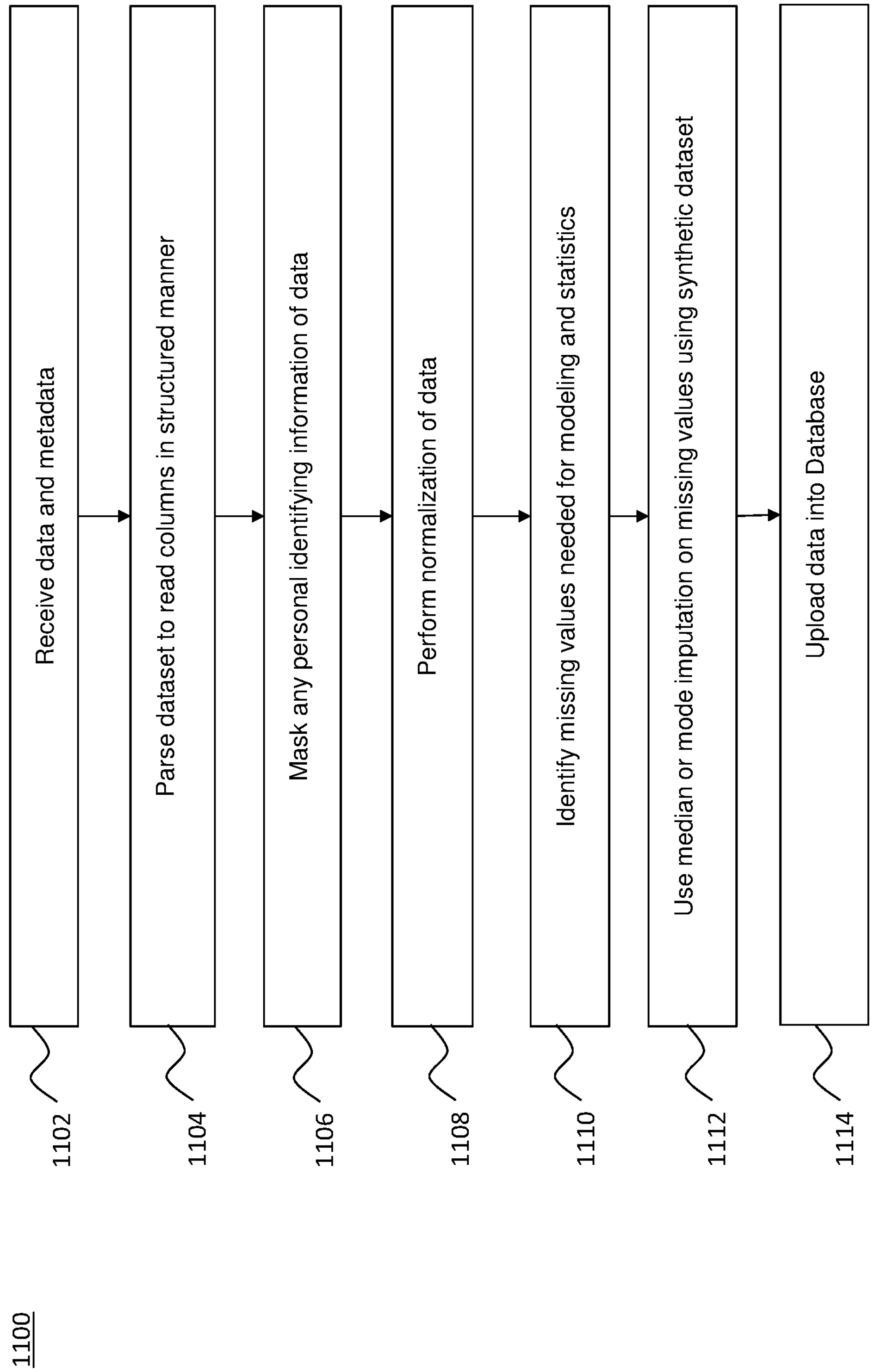
FIG. 11 illustrates a flow chart for generating a synthetic dataset for training predictive models, in accordance with various embodiments.

FIG. 11 illustrates a flow chart of a method 1100 for generating a synthetic dataset for training predictive models, in accordance with various embodiments. Method 1100 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1100 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1100 may include retrieving, editing, and/or storing files in a database that is part of, or is communicably coupled to, the computer, using, inter-glia, a trigger logic engine (e.g., databases 252). Methods consistent with the present disclosure may include at least some, but not all, of the steps illustrated in method 1100, performed in a different sequence. Furthermore, methods consistent with the present disclosure may include at least two or more steps as in method 1100 performed overlapping in time, or almost simultaneously.

Step 1102 includes receiving data and metadata from a healthcare center. For example, data pipeline engine 240 may request patient date from a healthcare center through an API. Furthermore, information on hospital machinery used to measure any or all patient data may be included.

Step 1104 includes parsing the received dataset to read columns in a structured manner that is compliant with database 252-1 schema rules.

Step 1106 includes masking personal identifying information from the received data. An example of this process may include a rule-based algorithm or a machine learning algorithm such as a long short-term memory network (LSTM) to identify data that may be PHI.

Step 1108 includes performing data normalization. For example, data pipeline engine 240 may normalize the local records from the healthcare facility using template records and normalization functions based on metadata associated with the local records.

Step 1110 includes identifying missing values needed for modeling and statistics. In various embodiments, step 1110 may include performing a (missing_values(data X)) function after reading the data that parses through each record and determines whether there are null values.

Step 1112 includes imputing missing values using synthetic dataset. For example, step 1112 may include using median or mode imputation, or other imputation techniques to generate missing values. Step 1114 includes uploading the synthetic data into the database.

Figure 12:
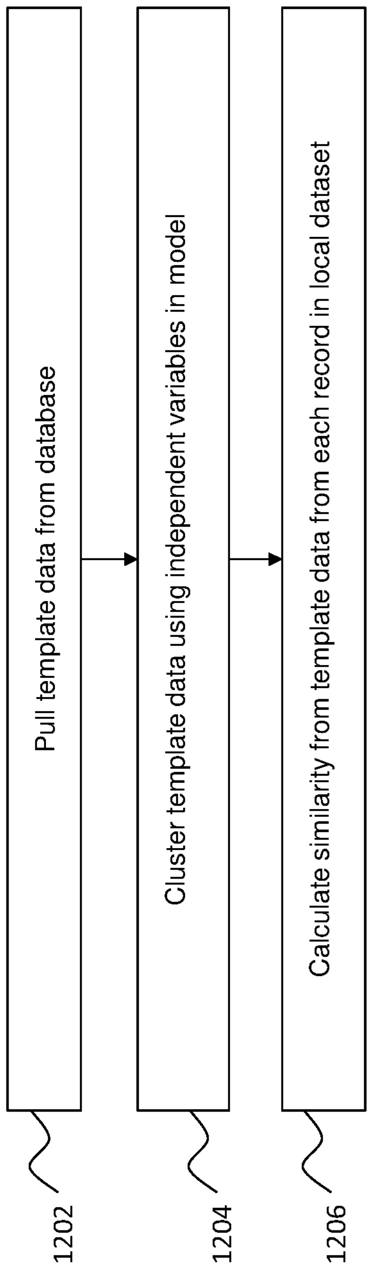
FIG. 12 illustrates a flow chart for determining similarity between local and template datasets, in accordance with various embodiments.

FIG. 12 illustrates a flow chart of a method 1200 for determining similarity between local and template datasets, in accordance with various embodiments. Method 1200 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1200 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1200 may include retrieving, editing, and/or storing files in a database that is part of, or is communicably coupled to, the computer, using, inter-alia, a trigger logic engine (e.g., databases 252). Methods consistent with the present disclosure may include at least some, but not all, of the steps illustrated in method 1200, performed in a different sequence. Furthermore, methods consistent with the present disclosure may include at least two or more steps as in method 1200 performed overlapping in time, or almost simultaneously.

Step 1202 includes pulling template data from a database. For example, data pipeline engine 240 may pull template records and/or models from database 252.

Step 1204 includes clustering template data using independent variables in model. For example, data for clustering template data may be pulled from database 252.

Step 1206 includes calculating similarity from template data from each record in local dataset. For example, as further described in connection with FIG. 18, data pipeline engine 240, and more specifically similarity tool 248, may determine distances between clusters of data in local and template datasets to determine similarity.

Figure 13:
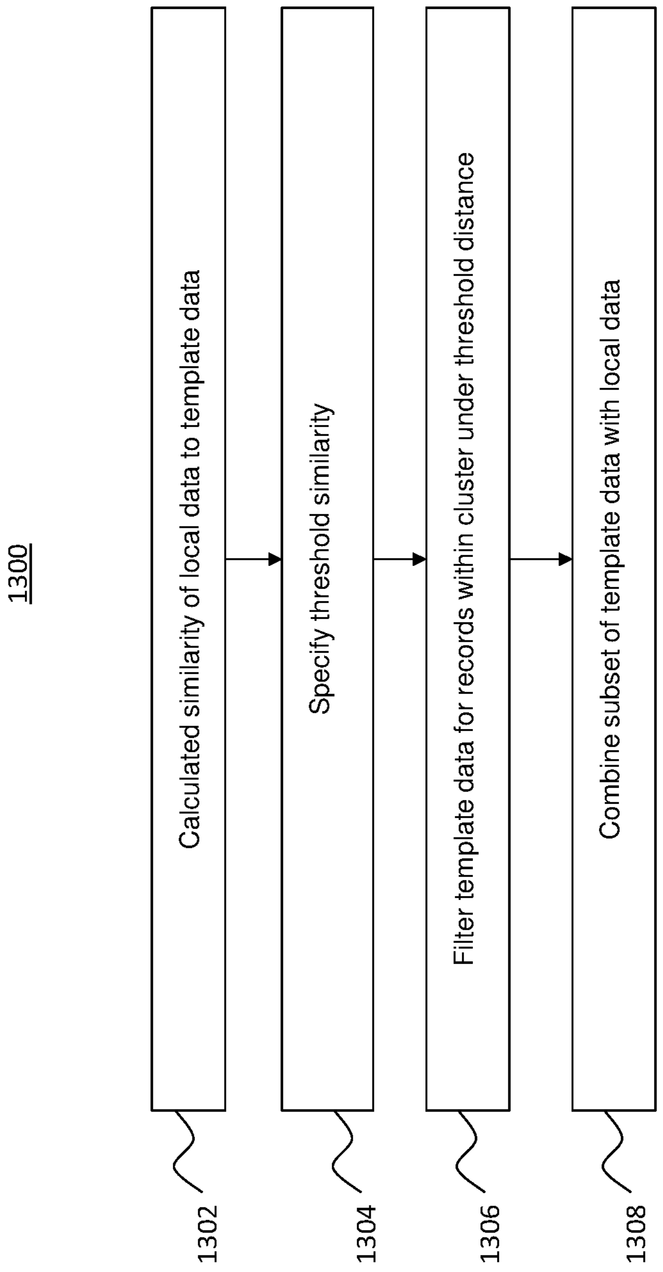
FIG. 13 illustrates a flow chart for combining local and template records in a synthetic dataset, in accordance with various embodiments.

FIG. 13 illustrates a flow chart of a method 1300 for combining local and template records in a synthetic dataset, in accordance with various embodiments. Method 1300 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1300 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1300 may include retrieving, editing, and/or storing files in a database that is part of, or is communicably coupled to, the computer, using, inter-glia, a trigger logic engine (e.g., databases 252). Methods consistent with the present disclosure may include at least some, but not all, of the steps illustrated in method 1300, performed in a different sequence. Furthermore, methods consistent with the present disclosure may include at least two or more steps as in method 1300 performed overlapping in time, or almost simultaneously.

Step 1302 includes calculating similarity of local data to template data. For example, as described in connection with FIG. 12, data pipeline engine 240 may determine similarity between datasets based on distances between clusters.

Step 1304 includes specifying a threshold similarity. The threshold similarity may be based on the target application and/or the quality of the training dataset and may be user defined. In such embodiments, the threshold similarity may be user defined.

Step 1306 includes discarding template data for records that pertain to clusters under threshold distance specified in step 1304. Step 1308 includes combining subset of template data with local data.

Figure 14:
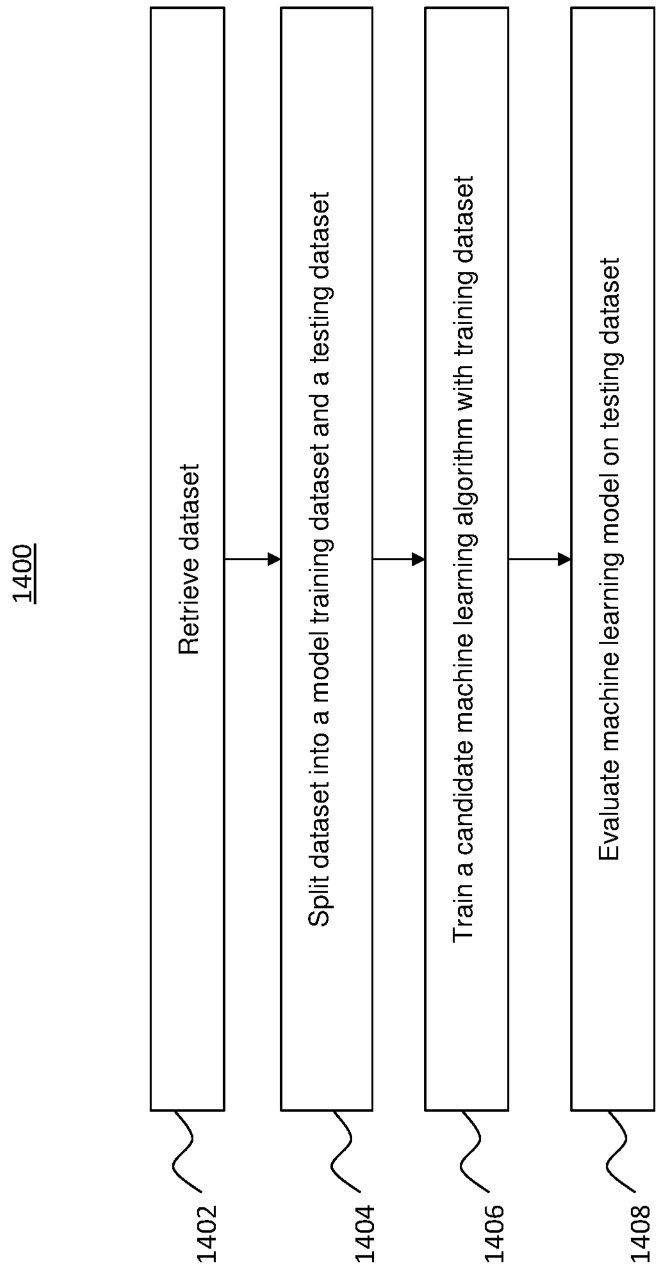
FIG. 14 illustrates a flow chart for evaluating a machine learning model using testing synthetic dataset, in accordance with various embodiments.

FIG. 14 illustrates a flow chart of a method 1400 for evaluating a machine learning model using testing synthetic dataset, in accordance with various embodiments. Method 1400 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1400 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1400 may include retrieving, editing, and/or storing files in a database that is part of, or is communicably coupled to, the computer, using, inter-alia, a trigger logic engine (e.g., databases 252). Methods consistent with the present disclosure may include at least some, but not all, of the steps illustrated in method 1400, performed in a different sequence. Furthermore, methods consistent with the present disclosure may include at least two or more steps as in method 1400 performed overlapping in time, or almost simultaneously.

Step 1402 includes retrieving a dataset from, for example, database 252.

Step 1404 includes splitting the dataset into a model training dataset and a testing dataset.

Step 1406 includes training a candidate machine learning algorithm with training dataset. An example machine learning model can be a neural network, or an ensemble machine learning model (not shown). The example machine learning model may be trained by using the model training dataset, user defined hyperparameter space using a cross-validated approach for a user defined number of iterations. The machine learning model may be chosen from a pre-defined list a user specifies.

Step 1408 includes evaluating machine learning model on testing dataset. For example, the evaluation may follow steps shown in FIG. 15.

FIG. 15 illustrates a flow chart of a method 1500 for training a machine learning model using training synthetic data, in accordance with various embodiments. Method 1500 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1500 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1500 may include retrieving, editing, and/or storing files in a database that is part of, or is communicably coupled to, the computer, using, inter-glia, a trigger logic engine (e.g., databases 252). Methods consistent with the present disclosure may include at least some, but not all, of the steps illustrated in method 1500, performed in a different sequence. Furthermore, methods consistent with the present disclosure may include at least two or more steps as in method 1500 performed overlapping in time, or almost simultaneously.

Step 1502 includes using trained model to generate predictions of test dataset. For example, trained model may be any model that is created or modified using a portion of the local or template data.

Step 1504 includes calculating AUROC, Sensitivity, Specificity, PPV, F1 Measure, and other machine learning metrics of test dataset. The calculations may be performed by the statistics tool 242.

Step 1506 includes calculating impact on Hospital KPI's such as mortality event within a user defined range, length of stay, readmission in a user defined range, or escalation of hospital department within a user defined range. An example metric could be readmission within 30 days, and identifying statistical significance of metric amongst predictions.

Step 1508 may include performing iterations for refining calculations of the hospital KPIs. Thus, step 1508 may include returning to step 1502 to generate additional predictions based on the dataset. However, if no additional iterations need to be performed, process may move from step 1508 to step 1510. The iteration criteria may be defined by completion of a user defined number of iterations, as well as a comparison to the template model applied to the local data.

Step 1510 includes identifying at least one model corresponding to best performance in calculated metrics and hospital KPI's. For example, the selection criteria may be using a weighted calculation of the calculated metrics and hospital KPI's (not shown).

Step 1512 includes training a final model on entirety of dataset. As previously discussed in connection with FIG. 6, the final model may be selected through a model selection logic.

Figure 16:
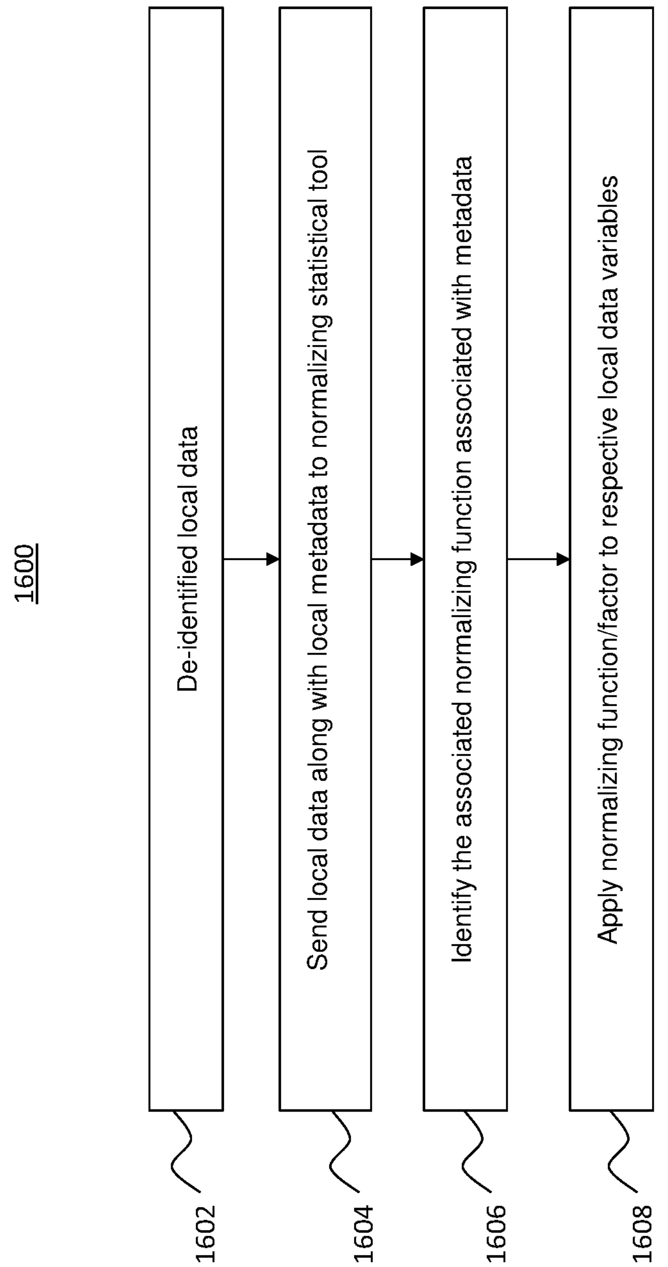
FIG. 16 illustrates a flow chart for normalizing local records, in accordance with various embodiments.

FIG. 16 illustrates a flow chart of a method 1600 for normalizing local records, in accordance with various embodiments. Method 1600 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1600 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1600 may include retrieving, editing, and/or storing files in a database that is part of, or is communicably coupled to, the computer, using, inter-alia, a trigger logic engine (e.g., databases 252). Methods consistent with the present disclosure may include at least some, but not all, of the steps illustrated in method 1600, performed in a different sequence. Furthermore, methods consistent with the present disclosure may include at least two or more steps as in method 1600 performed overlapping in time, or almost simultaneously.

Step 1602 includes de-identifying local data. For example, in step 1602 data masking tool 247 may de-identify local records of patients in a target healthcare facility.

Step 1604 includes sending local data along with local metadata to normalizing statistical tool 244. In various embodiments, statistical tool may receive data files including a plurality of metadata fields. For example, in step 1604 statistical tool 244 may receive biomarker records from a hospital, a clinical laboratory, or a research institute. Moreover, statistical tool 244 may identify and/or retrieving a template record for normalization, the template record including template metadata field. This can be accomplished by first extracting the test name from the input biomarker record and then retrieving from template memory 456 the entry with the corresponding test name. Further, statistical tool 244 may generate a normalization vector including mismatching biomarker records that have metadata fields different from the template. The normalization vector can be formed by performing an iterative comparison between each metadata field, determining if they are equal, and setting the value for a specific field to '1' if so and to '0' if not. The normalization vector is then of the format: {field1: 1/0, field2: 1/0, . . . , fieldN: 1/0}.

Step 1606 includes identifying the associated normalizing function associated with metadata. For instance, step 1606 may include parsing metadata fields in biomarker records data and comparing the number of metadata fields between records data and template data. For example, statistical tool 244 may read metadata fields in local records and compare number of metadata fields in received biomarker records with samples stored in template memory. Additionally, step 1606 may include a determination of whether the number of metadata fields are the same and select an adjustment function when the metadata fields are not the same.

Step 1608 includes applying a normalizing function/factor to respective local data variables. For example, step 1608 may include modifying data fields of biomarker records in the normalization vector by applying the adjustment functions. Specifically, for each metadata field name in the normalization vector, check if the value equals '1', and if it does, then identify and/or retrieve the corresponding adjustment function. For instance, given the biomarker record, extract the test name and then that test name combined with the corresponding metadata field can be used as index into Adjust Functions, which can then output the corresponding adjustment function. After the adjustment function is retrieved, it may then be applied to the biomarker record.

Figure 17:
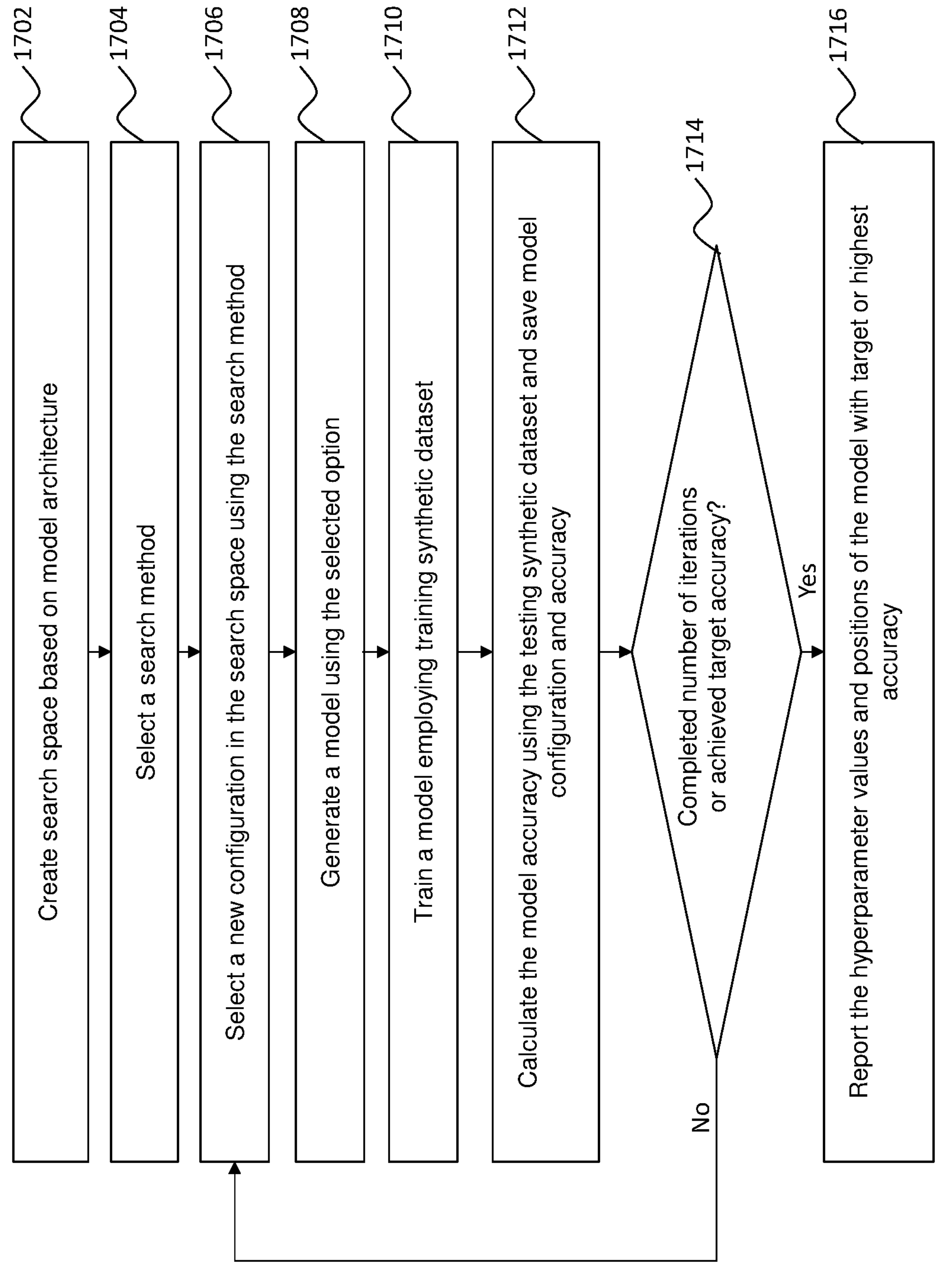
FIG. 17 illustrates a flow chart for tuning hyperparameters in a machine learning model, in accordance with various embodiments.

FIG. 17 illustrates a flow chart of a method 1700 for tuning hyperparameters in a machine learning model, in accordance with various embodiments. Method 1700 may be performed at least partially by any one of client devices coupled to one or more servers through a network (e.g., any one of servers 130 and any one of client devices 110, and network 150). For example, in accordance with various embodiments, the servers may host one or more medical devices or portable computer devices carried by medical or healthcare personnel. Client devices 110 may be handled by a user such as a worker or other personnel in a healthcare facility, or a paramedic in an ambulance carrying a patient to the emergency room of a healthcare facility or hospital, an ambulance, or attending to a patient at a private residence or in a public location remote to the healthcare facility. At least some of the steps in method 1700 may be performed by a computer having a processor executing commands stored in a memory of the computer (e.g., processors 212 and memories 220). In accordance with various embodiments, the user may activate an application in the client device to access, through the network, a data pipeline engine in the server (e.g., application 222 and data pipeline engine 240). The data pipeline engine may include a modeling tool, a statistics tool, a data parsing tool, a data masking tool, and a similarity tool (e.g., modeling tool 242, statistics tool 244, a data parsing tool 246, a data masking tool 247, and a similarity tool 248) to retrieve, supply, and process clinical data in real-time, and provide training data sets for forming ML models.

Further, steps as disclosed in method 1700 may include retrieving, editing, and/or storing files in a database that is part of, or is communicably coupled to, the computer, using, inter-alia, a trigger logic engine (e.g., databases 252). Methods consistent with the present disclosure may include at least some, but not all, of the steps illustrated in method 1700, performed in a different sequence. Furthermore, methods consistent with the present disclosure may include at least two or more steps as in method 1700 performed overlapping in time, or almost simultaneously.

Step 1702 includes creating search space based on model architecture. For example, in step 1702 data pipeline engine 240 may define a hyperparameter space. Step 1704 includes selecting a search method, which may include one or more of a grid search, a random search, Bayesian optimization, or evolutionary optimization. Step 1706 includes selecting a new configuration in the hyperparameter search space using the selected search method of step 1704. For instance, data pipeline engine 240 may perform Bayesian optimization to identify a combination of hyperparameters for a candidate ML model. And step 1708 includes generating a model using the selected option.

Step 1710 includes training a model employing training synthetic dataset. For example, modeling tool 242 may generate an ensemble machine learning model based on a synthetic training dataset that combines local records of a healthcare facility with template records. Step 1712 includes calculating the model accuracy using the testing synthetic dataset and save model configuration and accuracy.

Step 1714 includes determining whether method 1700 has completed a target number of iterations or the model evaluated in step 1712 achieved a target accuracy. If the target number of iterations has not been completed or the model did not achieve target accuracy (Step 1714: No), method 1700 may return to step 1706 to select a new configuration in the search space to test a different hyper-parameter combination. However, if the target number of iterations was completed or the model achieved that target accuracy (Step 1714: Yes), method 1700 may continue to step 1716.

Step 1716 includes reporting the hyperparameter values and positions of the model with target or highest accuracy. The target may include metrics identified in FIG. 15.

Figure 18:
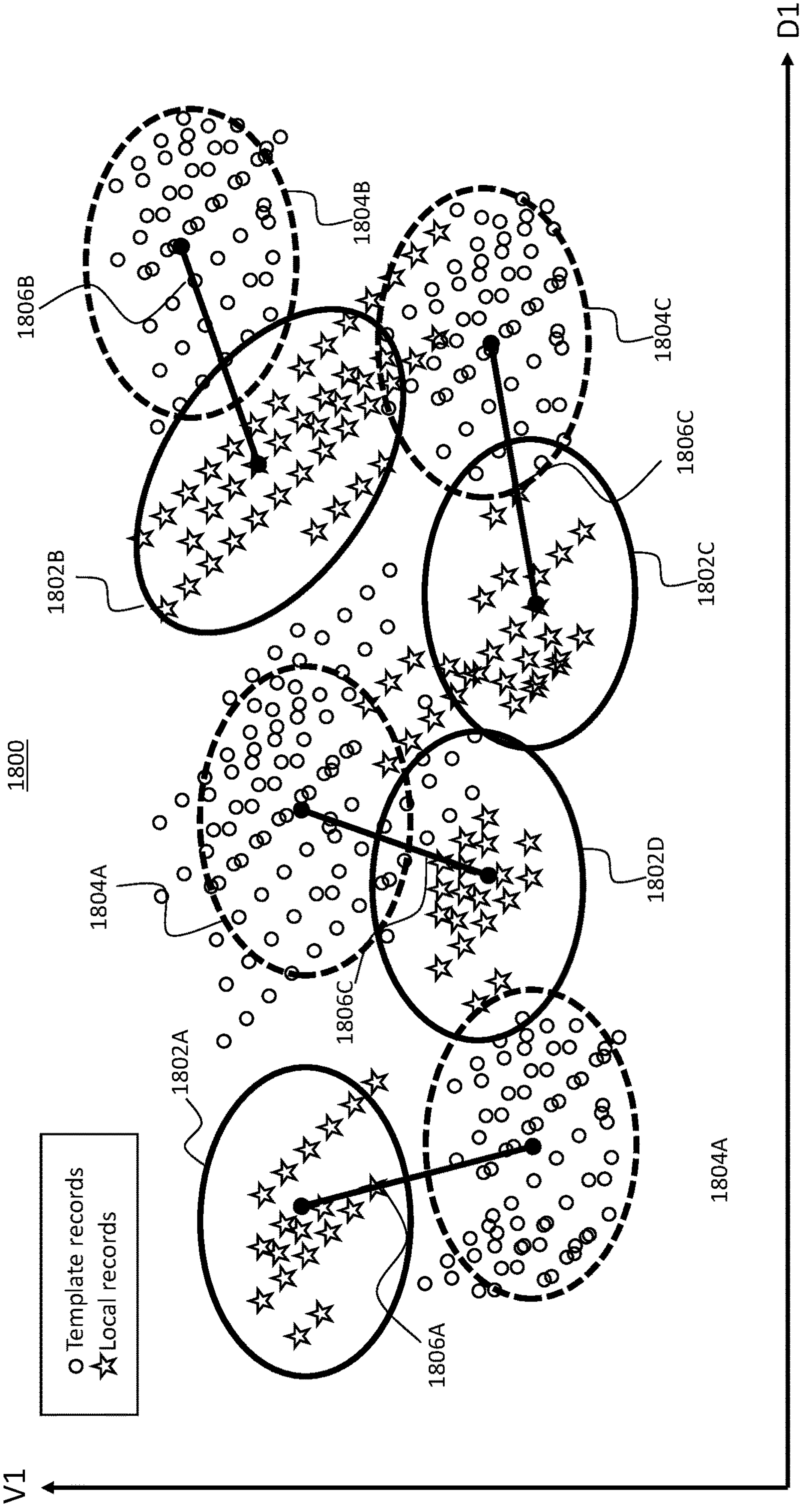
FIG. 18 shows a graphical representation of clustered local and template records, in accordance with various embodiments.

FIG. 18 shows a graphical representation 1800 of clustered local and template records, in accordance with various embodiments. Graphical representation 1800 shows a template records and local records organized for a dimension and value. Graphical representation 1800 shows local clusters 1802A, 1802B, 1802C, and 1802D. Local clusters 1802A-D may group local records that are within a distance of a centroid. In various embodiments, one or more processors 212 may perform clustering operations such as hierarchical clustering, Fuzzy clustering, density-based clustering, or model-based clustering to generate local clusters 1802A-D.

Similarly, graphical representation 1800 shows template clusters 1804A, 1804B, 1804C, and 1804D. Template clusters 1804A-D may group local records that are within a distance of a centroid. Like with local clusters 1802A-D, processors 212 may generate template clusters 1804A-D using clustering techniques such as hierarchical clustering, Fuzzy clustering, density-based clustering, or model-based clustering.

Graphical representation 1800 also shows cluster distances 1806A, 1806B, 1806C, and 1806D. Cluster distances 1806A-D may be estimated by similarity defining tool 248. As explained in connection with FIG. 12, similarity defining tool 248 may calculate similarity to template data from each record in a local dataset based on cluster distances 1806A-D. In various embodiments, the generation of synthetic records and synthetic datasets may be generated based on cluster distances 1806A-D.

Figure 19:
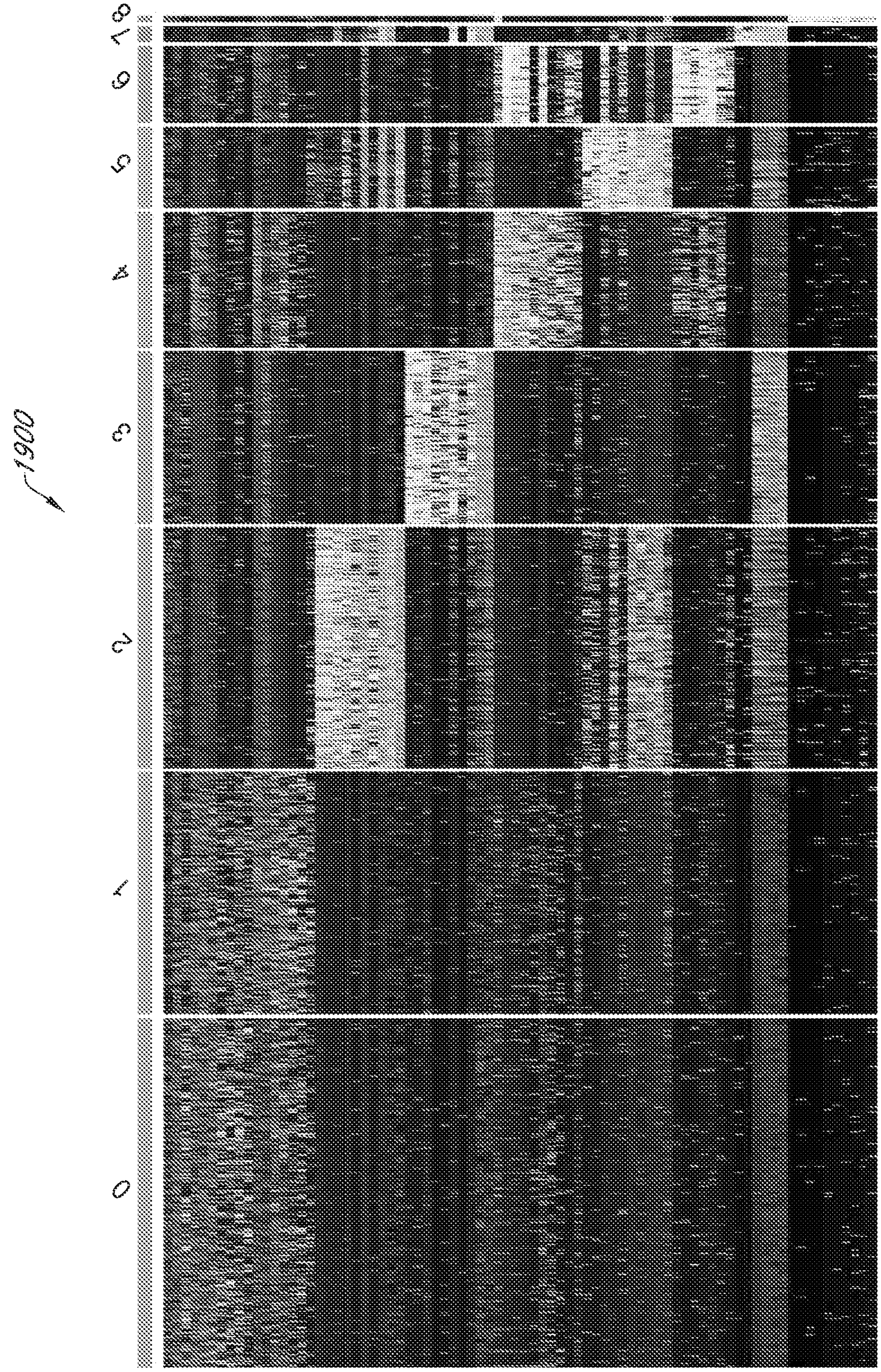
FIG. 19 shows a graphical representation of record clustering, in accordance with various embodiments.

FIG. 19 shows a graphical representation 1900 of record clustering, in accordance with various embodiments. In representation 1900, the numbers on the top indicate groupings. The y axis would pertain to different columns in the dataset, and the x axis would be increments of patient records. The tone indicates the magnitude of the value for the record and patient.

Figure 20:
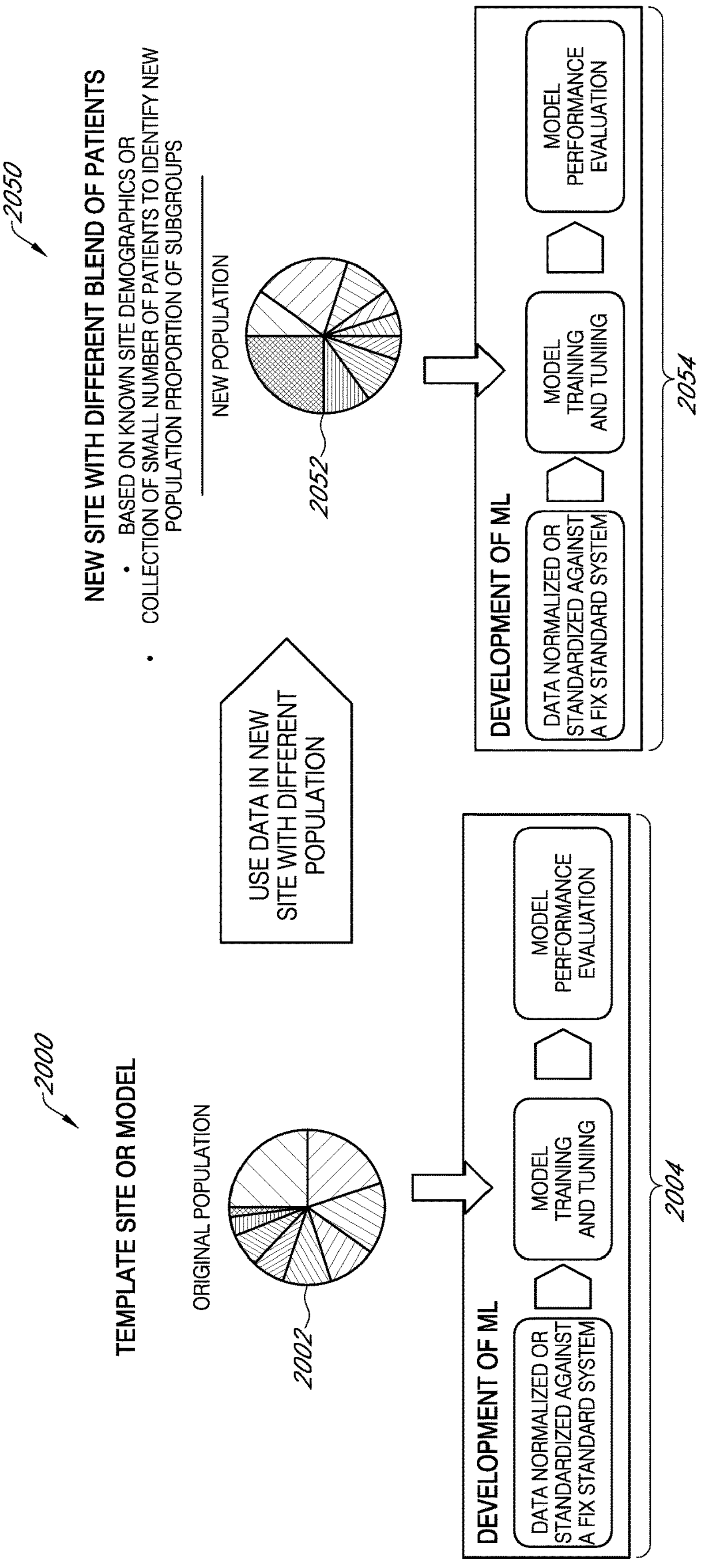
FIG. 20 shows a graphical representation of development of a machine learning model using a synthetic training dataset, in accordance with various embodiments.

FIG. 20 shows a graphical representation 2000 of machine learning model training using a synthetic training dataset, in accordance with various embodiments. Graphical representation 2000 shows a standard process 2000 that trains an ML model with an original population 2002. As shown in FIG. 20, in process 2000 ML models may be generated through a sequence 2004 of normalizing data, training and tuning the model, and then performing model evaluation. Process 2000 modeling may be used for a healthcare facility with a complete training dataset.

Graphical representation 2000 also shows an enhanced process 2050 in which an ML model is trained with a different new population 2052. In various embodiments, new population 2052 would be insufficient for training an ML model. For example, new population 2052 may not include enough number of samples. However, as previously discussed, data pipeline engine 240 may use original population 2002 and combine it with new population 2052 to create a synthetic dataset based on identified demographics and/or the determination of subgroups. The synthetic dataset may allow the development of models with a modified modeling sequence 2054.

Figure 21:
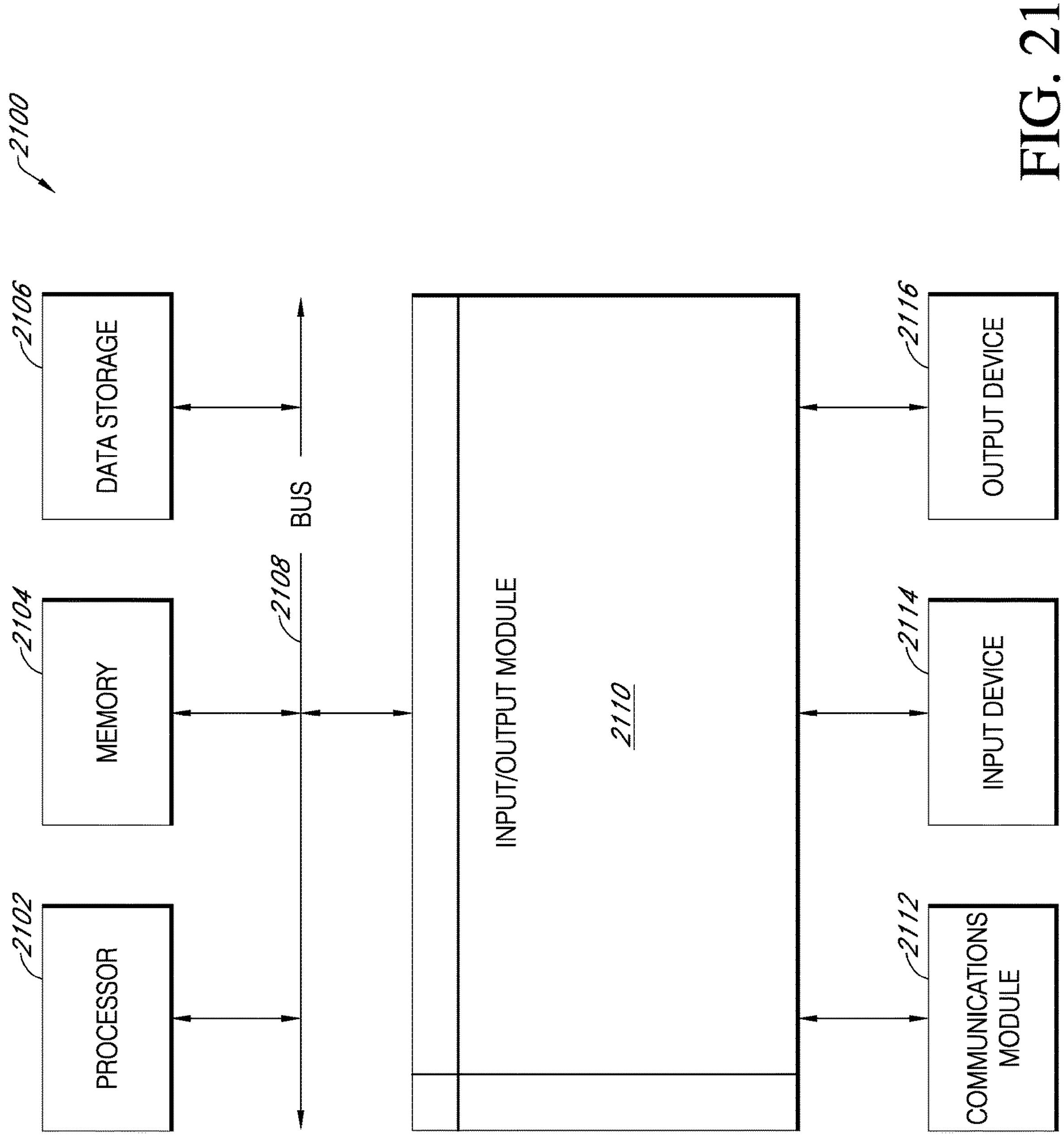
FIG. 21 is a block diagram illustrating an example computer system with which the client and server of FIGS. 1 and 2, and the methods of FIGS. 9-17 can be implemented, in accordance with various embodiments.

FIG. 21 is a block diagram illustrating an exemplary computer system 2100 with which the client device 110 and server 130 of FIGS. 1 and 2, and the methods described in FIGS. 9-17 can be implemented. In various aspects, the computer system 2100 may be implemented using hardware or a combination of software and hardware, either in a dedicated server, or integrated into another entity, or distributed across multiple entities.

Computer system 2100 (e.g., client device 110 and server 130) includes a bus 2108 or other communication mechanism for communicating information, and a processor 2102 (e.g., processors 212) coupled with bus 2108 for processing information. By way of example, the computer system 2100 may be implemented with one or more processors 2102. Processor 2102 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 2100 can include, in addition to hardware, code that creates an execution environment for the computer program in question, e.g., code that constitutes processor firmware, a protocol stack, a database management system, an operating system, or a combination of one or more of them stored in an included memory 2104 (e.g., memories 220), such as a Random Access Memory (RAM), a flash memory, a Read-Only Memory (ROM), a Programmable Read-Only Memory (PROM), an Erasable PROM (EPROM), registers, a hard disk, a removable disk, a CD-ROM, a DVD, or any other suitable storage device, coupled to bus 2108 for storing information and instructions to be executed by processor 2102. The processor 2102 and the memory 2104 can be supplemented by, or incorporated in, special purpose logic circuitry.

The instructions may be stored in the memory 2104 and implemented in one or more computer program products, i.e., one or more modules of computer program instructions encoded on a computer-readable medium for execution by, or to control the operation of, the computer system 2100, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multi paradigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, with languages, and xml-based languages. Memory 2104 may also be used for storing temporary variables or other intermediate information during execution of instructions to be executed by processor 2102.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 2100 further includes a data storage device 1406 such as a magnetic disk or optical disk, coupled to bus 2108 for storing information and instructions. Computer system 2100 may be coupled via input/output module 2110 to various devices. Input/output module 2110 can be any input/output module. Exemplary input/output modules 2110 include data ports such as USB ports. The input/output module 2110 is configured to connect to a communications module 2112. Exemplary communications modules 2112 (e.g., communications modules 218) include networking interface cards, such as Ethernet cards and modems. In various aspects, input/output module 2110 is configured to connect to a plurality of devices, such as an input device 2114 (e.g., input device 214) and/or an output device 2116 (e.g., output device 216). Exemplary input devices 2114 include a keyboard and a pointing device, e.g., a mouse or a trackball, by which a user can provide input to the computer system 2100. Other kinds of input devices 2114 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices 2116 include display devices, such as an LCD (liquid crystal display) monitor, for displaying information to the user.

According to one aspect of the present disclosure, the client device 110 and server 130 can be implemented using a computer system 2100 in response to processor 2102 executing one or more sequences of one or more instructions contained in memory 1404. Such instructions may be read into memory 2104 from another machine-readable medium, such as data storage device 2106. Execution of the sequences of instructions contained in main memory 2104 causes processor 2102 to perform the process steps described herein. One or more processors in a multi-processing arrangement may also be employed to execute the sequences of instructions contained in memory 1404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 2100 can include clients and servers. A client and server are generally remote from each other and typically interact through a communication network. The relationship of client and server arises by virtue of computer programs running on the respective computers and having a client-server relationship to each other. Computer system 2100 can be, for example, and without limitation, a desktop computer, laptop computer, or tablet computer. Computer system 2100 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer-readable medium" as used herein refers to any medium or media that participates in providing instructions to processor 2102 for execution. Such a medium may take many forms, including, but not limited to, non-volatile media, volatile media, and transmission media. Non-volatile media include, for example, optical or magnetic disks, such as data storage device 1406. Volatile media include dynamic memory, such as memory 2104. Transmission media include coaxial cables, copper wire, and fiber optics, including the wires that include bus 2108. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

Figure 22:
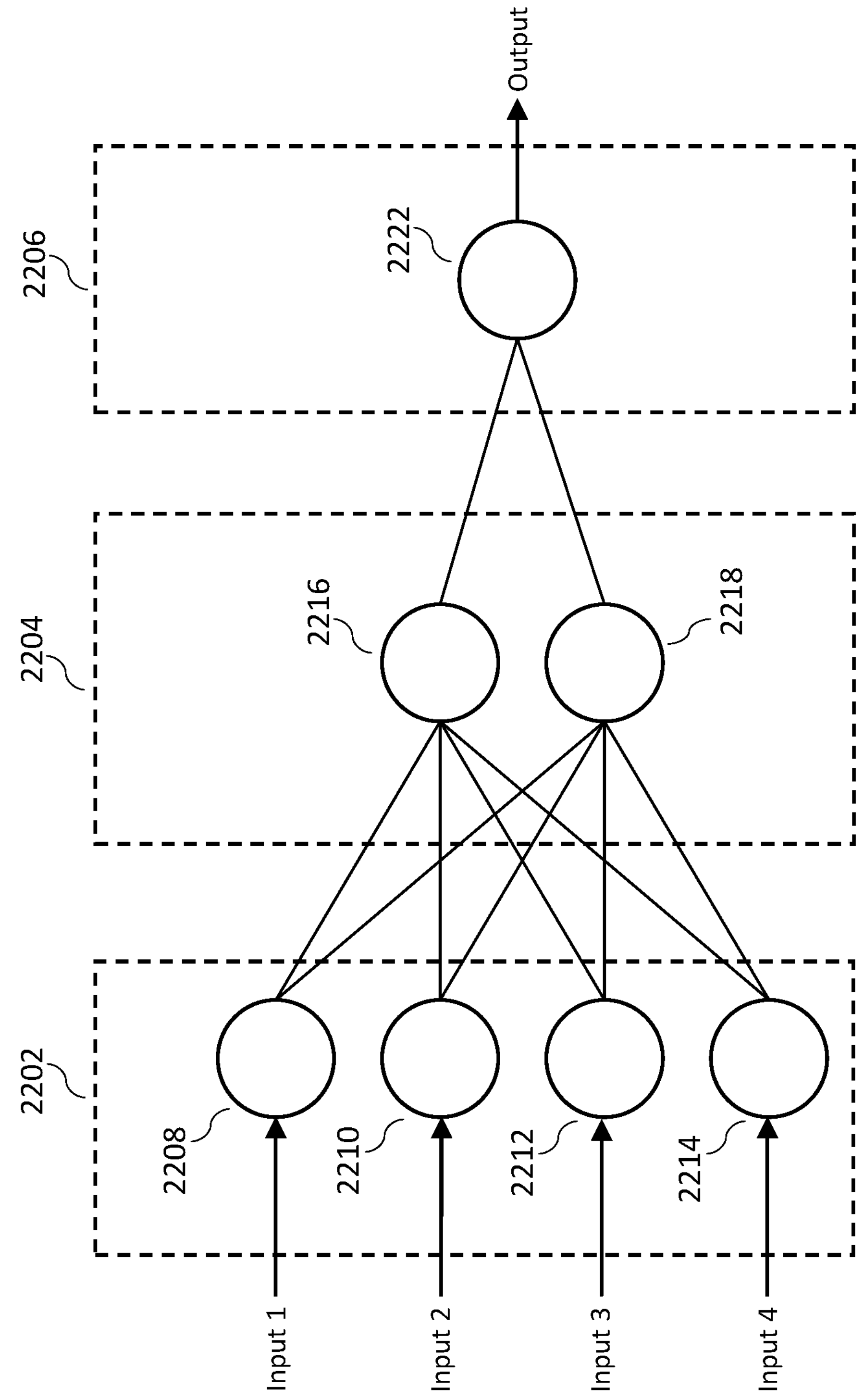
FIG. 22 illustrates an example neural network that can be used to implement a machine learning model, in accordance with various embodiments.

FIG. 22 illustrates an example neural network that can be used to implement the machine learning model according to various embodiments of the present disclosure. It is to be understood that FIG. 22 is a non-limiting example illustration and that other types of neural networks or AI/ML algorithms can be used to implement the machine learning models according to the various embodiments of the present disclosure.

As shown, the artificial neural network 2200 includes three layers—an input layer 2202, a hidden layer 2204, and an output layer 2206. Each of the layers 2202, 2204, and 2206 may include one or more nodes. For example, the input layer 2202 includes nodes 2208-2214, the hidden layer 2204 includes nodes 2216-2218, and the output layer 2206 includes a node 2222. In this example, each node in a layer is connected to every node in an adjacent layer. For example, the node 2208 in the input layer 2202 is connected to both of the nodes 2216, 2218 in the hidden layer 2204. Similarly, the node 2216 in the hidden layer is connected to all of the nodes 2208-2214 in the input layer 2202 and the node 2222 in the output layer 2206. Although only one hidden layer is shown for the neural network 2200, it has been contemplated that the neural network 2200 used to implement the machine learning model disclosed herein may include as many hidden layers as necessary or desired.

In this example, the neural network 2200 receives a set of input values and produces an output value. Each node in the input layer 2202 may correspond to a distinct input value. For example, when the neural network 2200 is used to implement the machine learning model disclosed herein, each node in the input layer 2202 may correspond to the input data {Xi(tx)}.

In various embodiments, each of the nodes 2216-2218 in the hidden layer 2204 generates a representation, which may include a mathematical computation (or algorithm) that produces a value based on the input values received from the nodes 2208-2214. The mathematical computation may include assigning different weights to each of the data values received from the nodes 2208-2214. The nodes 2216 and 2218 may include different algorithms and/or different weights assigned to the data variables from the nodes 2208-2214 such that each of the nodes 2216-2218 may produce a different value based on the same input values received from the nodes 2208-2214. In various embodiments, the weights that are initially assigned to the features (or input values) for each of the nodes 2216-2218 may be randomly generated (e.g., using a computer randomizer). The values generated by the nodes 2216 and 2218 may be used by the node 2222 in the output layer 2206 to produce an output value for the neural network 2200. When the neural network 2200 is used to implement the machine learning model disclosed herein, the output value produced by the neural network 2200 may indicate the imputed data {Yi(tx)}.

The neural network 2200 may be trained by using training data. For example, the training data herein may be training dataset from the training database 252-2. By providing training data to the neural network 2200, the nodes 2216-2218 in the hidden layer 2204 may be trained (adjusted) such that an optimal output is produced in the output layer 2206 based on the training data. By continuously providing different sets of training data, and penalizing the neural network 2200 when the output of the neural network 2200 is incorrect, the neural network 2200 (and specifically, the representations of the nodes in the hidden layer 2204) may be trained (adjusted) to improve its performance in data normalization. Adjusting the neural network 2200 may include adjusting the weights associated with each node in the hidden layer 2204.

Although the above discussions pertain to a neural network as an example of a machine learning model, it is understood that other types of AI/ML methods may also be suitable to implement the various aspects of the present disclosure. For example, support vector machines (SVMs) may be used to implement machine learning. SVMs are a set of related supervised learning methods used for classification and regression. A SVM training algorithm—which may be a non-probabilistic binary linear classifier—may build a model that predicts whether a new example falls into one category or another. As another example, Bayesian networks may be used to implement machine learning. A Bayesian network is an acyclic probabilistic graphical model that represents a set of random variables and their conditional independence with a directed acyclic graph (DAG). The Bayesian network could present the probabilistic relationship between one variable and another variable. Another example is a machine learning engine that employs a decision tree learning model to conduct the machine learning process. In some instances, decision tree learning models may include classification tree models, as well as regression tree models. In various embodiments, the machine learning engine employs a Gradient Boosting Machine (GBM) model (e.g., XGBoost) as a regression tree model. Other machine learning techniques may be used to implement the machine learning engine, for example via Random Forest or Deep Neural Networks. Other types of machine learning algorithms are not discussed in detail herein for reasons of simplicity and it is understood that the present disclosure is not limited to a particular type of machine learning.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C. To the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Various features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in various combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In various circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products. Other variations are within the scope of the following claims.

RECITATIONS OF VARIOUS EMBODIMENTS OF THE PRESENT DISCLOSURE

Embodiment 1: A comprising: receiving, from a healthcare facility, a local dataset comprising local records of first patients associated with the healthcare facility; retrieving, from a database, a template dataset comprising template records, the template records organized in clusters comprising variable centroids; calculating a similarity metric between the local records and the template records by comparing demographics and the variable centroids; generating a synthetic dataset by combining at least a portion of the template records and at least a portion of the local records, the portion of the template records selected based on a threshold similarity; segregating the synthetic dataset into a training synthetic dataset and a testing synthetic dataset; and generating the machine learning predictive model by: performing at least one of tuning a template model according to the training synthetic dataset or generating a new predictive model; and validating the tuned template model or the new predictive model employing the testing synthetic dataset.

Embodiment 2: The method of embodiment 1, wherein data streams are processed in real time by a data parsing tool and the local records are deidentified by the data masking tool.

Embodiment 3: The method of embodiment 1 or 2, wherein the database comprises previously trained models, the template records, and model evaluation metrics.

Embodiment 4: The method of any of embodiments 1-3, wherein the generating the synthetic dataset comprises identifying missing clusters in the local dataset that are present in the template dataset.

Embodiment 5: The method of any of embodiments 1-4, wherein: the validating the tuned template model or the new predictive model comprises adjusting hyperparameters based on hospital key performance indicators (KPIs).

Embodiment 6: The method of any of embodiments 1-5, further comprising performing a clustering function to generate the clusters based on the template records, the performing the clustering including performing data normalization.

Embodiment 7: The method of any of embodiments 1-6, wherein the generating the machine learning predictive model further comprises: generating a first tuned model by tailoring the template model using the local records as training data; generating a second tuned model by tailoring the template model using the training synthetic data; generating a first new model using the local records as training data; generating a second new model using the training synthetic dataset; and comparing the first tuned model, the second tuned model, the first new model, and the second new model to determine a highest evaluated model.

Embodiment 8: The method of embodiment 7, wherein the comparing the first tuned model, the second tuned model, the first new model, and the second new model comprises selecting a final model based on weighted KPIs of the first tuned model, the second tuned model, the first new model, and the second new model.

Embodiment 9: The method of any of embodiments 1-8, wherein the generating the synthetic dataset comprises generating additional records based on the local records using median or mode imputation.

Embodiment 10: The method of any of embodiments 1-9, wherein the generating the synthetic dataset comprises employing a Bayesian model to generate testing database on the local records.

Embodiment 11: The method of any of embodiments 1-10, wherein the tuned template model and the new predictive model provide an initial treatment prediction for providing treatment to patients.

Embodiment 12: The method of any of embodiments 1-11, wherein the local records and the template records comprise patient biomarker information retrieved from electronic health records of the healthcare facility.

Embodiment 13: The method of any of embodiments 1-12, further comprising transmitting model results to the healthcare facility through a fast healthcare interoperability resources application programing interface.

Embodiment 14: The method of embodiment 11, further comprising assigning a treatment protocol for the providing treatment to second patients based on the initial treatment prediction, each treatment protocol being optimized based on the tuned template model and the new predictive model.

Embodiment 15: The method of any of embodiments 1-14, wherein the synthetic dataset is larger than the local dataset.

Embodiment 16: The method of any of embodiments 1-15, further comprising performing a clustering function to generate the clusters based on the template records, wherein the local records comprise biomarker records comprising a plurality of biomarker metadata fields; and the performing the clustering function comprises: generating a normalization vector comprising biomarker records including mismatching metadata fields that mismatch one or more of a plurality of template metadata fields in the template records; identifying adjustment functions for of the mismatching metadata fields; modifying data fields of biomarker records in the normalization vector by applying the adjustment functions to the data fields corresponding to the mismatching metadata fields; and generating a normalized data file comprising the modified biomarker records.

Embodiment 17: The method of any of embodiments 1-16, wherein the performing the at least one of tuning the template model according to the training synthetic dataset or generating the new predictive model comprises generating a model predicting probability of dysregulated host response caused by infection.

Embodiment 18: The method of any of embodiments 1-17, wherein the operations further comprise: employing a statistics tool to generate model metrics; and storing the model metrics in the database.

Embodiment 19: The method of embodiment 5, wherein the hospital KPIs include one or both of a critical care outcome indicator or a diagnostic indicator.

Embodiment 20: The method of embodiment 19, wherein the critical care outcome indicator includes one or more of a patient readmission rate, a mortality rate, an intensive care unit (ICU) escalation, number of patient ventilator free days, number of patient ventilator days, number of patient vasopressor days, or length of stay at hospital.

Embodiment 21: The method of embodiment 19 or 20, wherein the diagnostic indicator includes a positive predictive value (PPV), a negative predictive value (NPV), sensitivity, specificity, a true positive rate (TPR), or a false positive rate (FPR), of diagnoses performed at hospital.

Embodiment 22: A system, comprising: one or more memory devices; and one or more processors coupled to the one or more memory devices storing instructions that configure the one or more processors to perform the methods of embodiments 1-21.

Embodiment 23: A non-transitory computer-readable medium (CRM) storing instructions that when executed by one or more processors, cause the one or more processors to perform the methods of embodiments 1-21.

What is claimed is:

1. A system for generating a machine learning predictive model, the system comprising:
- one or more processors; and
- one or more memory devices storing instructions that configure the one or more processors to perform operations comprising:
  - receiving, from a healthcare facility, a local dataset comprising local records of first patients associated with the healthcare facility, wherein the local dataset comprises an original population depicted in a graphical user interface (GUI) a first demographic visual representation;
  - retrieving, from a database, a template dataset comprising template records, the template records organized in clusters comprising variable centroids;
  - calculating a similarity metric between the local records and the template records by comparing the original population and the variable centroids;
  - generating a synthetic dataset by combining at least a portion of the template records and at least a portion of the local records, the portion of the template records selected based on a threshold similarity;
  - outputting in the GUI a second demographic visual representation based on the synthetic dataset showing a new population comprising a set of blend of patients that is different from the original population;
  - segregating the synthetic dataset into a training synthetic dataset and a testing synthetic dataset; and
  - generating the machine learning predictive model by:
    - performing at least one of tuning a template model according to the training synthetic dataset or generating a new predictive model; and
    - validating the tuned template model or the new predictive model employing the testing synthetic dataset.

2. The system of claim 1, wherein the one or more processors comprise a data pipeline engine comprising a data parsing tool and a data masking tool, the data parsing tool being configured to process data streams in real time, the data masking tool being configured to deidentify the local records.

3. The system of claim 1, wherein the database comprises previously trained models, the template records, and model evaluation metrics.

4. The system of claim 1, wherein the generating the synthetic dataset comprises identifying missing clusters in the local dataset that are present in the template dataset.

5. The system of claim 1, wherein: the validating the tuned template model or the new predictive model comprises adjusting hyperparameters based on hospital key performance indicators (KPIs).

6. The system of claim 1, wherein the operations further comprise performing a clustering function to generate the clusters based on the template records, the performing the clustering including performing data normalization.

7. The system of claim 1, wherein the generating the machine learning predictive model further comprises:
- generating a first tuned model by tailoring the template model using the local records as training data;
- generating a second tuned model by tailoring the template model using the training synthetic data;
- generating a first new model using the local records as training data;
- generating a second new model using the training synthetic dataset; and
- comparing the first tuned model, the second tuned model, the first new model, and the second new model to determine a highest evaluated model.

8. The system of claim 7, wherein the comparing the first tuned model, the second tuned model, the first new model, and the second new model comprises selecting a final model based on weighted KPIs of the first tuned model, the second tuned model, the first new model, and the second new model.

9. The system of claim 1, wherein the generating the synthetic dataset comprises generating additional records based on the local records using median or mode imputation.

10. The system of claim 1, wherein the generating the synthetic dataset comprises employing a Bayesian model to generate testing database on the local records.

11. The system of claim 1, wherein the tuned template model and the new predictive model provide an initial treatment prediction for providing treatment to patients.

12. The system of claim 1, wherein the local records and the template records comprise patient biomarker information retrieved from electronic health records of the healthcare facility.

13. The system of claim 1, wherein the operations further comprise:
- transmitting model results to the healthcare facility through a fast healthcare interoperability resources application programing interface.

14. The system of claim 11, wherein the operations further comprise:
- assigning a treatment protocol for providing treatment to second patients based on the initial treatment prediction, each treatment protocol being optimized based on the tuned template model and the new predictive model.

15. The system of claim 1, wherein the synthetic dataset is larger than the local dataset.

16. The system of claim 1, wherein:

the operations further comprise performing a clustering function to generate the clusters based on the template records;

the local records comprise biomarker records comprising a plurality of biomarker metadata fields; and the performing the clustering function comprises:

generating a normalization vector comprising biomarker records including mismatching metadata fields that mismatch one or more of a plurality of template metadata fields in the template records;

identifying adjustment functions for the mismatching metadata fields;

modifying data fields of biomarker records in the normalization vector by applying the adjustment functions to the data fields corresponding to the mismatching metadata fields; and generating a normalized data file comprising the modified biomarker records.

17. The system of claim 1, wherein the performing the at least one of tuning the template model according to the training synthetic dataset or generating the new predictive model comprises generating a model predicting probability of dysregulated host response caused by infection.

18. The system of claim 1, wherein the operations further comprise:

employing a statistics tool to generate model metrics; and storing the model metrics in the database.

19. A computer-implemented method for generating a machine learning predictive model to a specific population, the method comprising:

receiving, from a healthcare facility, a local dataset comprising local records of patients associated with the healthcare facility, wherein the local dataset comprises an original population depicted in a graphical user interface (GUI) a first demographic visual representation;

retrieving, from a database, a template dataset comprising template records, the template records organized in clusters comprising variable centroids;

calculating a similarity metric between the local records and the template records by comparing the original population and the variable centroids;

generating a synthetic dataset by combining at least a portion of the template records and at least a portion of the local records, the portion of the template records selected based on a threshold similarity;

outputting in the GUI a second demographic visual representation based on the synthetic dataset showing a new population comprising a set of blend of patients that is different from the original population;

segregating the synthetic dataset into a training synthetic dataset and a testing synthetic dataset; and generating the machine learning predictive model by:

performing at least one of tuning a template model according to the training synthetic dataset or generating a new predictive model; and validating the tuned template model or the new predictive model employing the testing synthetic dataset.

20. A computer-implemented apparatus comprising:

at least one processor; and at least one memory device that configures the at least one processor to:

receive, from a healthcare facility, a local dataset comprising local records of patients associated with the healthcare facility, wherein the local dataset comprises an original population depicted in a graphical user interface (GUI) a first demographic visual representation;

retrieve, from a database, a template dataset comprising template records, the template records being organized in clusters comprising variable centroids;

calculate a similarity metric between the local records and the template records by comparing the original population and the variable centroids;

generate a synthetic dataset by combining at least a portion of the template records and at least a portion of the local records, the portion of the template records being selected based on a threshold similarity;

output in the GUI a second demographic visual representation based on the synthetic dataset showing a new population comprising a set of blend of patients that is different from the original population;

segregate the synthetic dataset into a training synthetic dataset and a testing synthetic dataset; and generate a machine learning predictive model by:

performing at least one of tuning a template model according to the training synthetic dataset or generating a new predictive model; and validating the tuned template model or the new predictive model employing the testing synthetic dataset.

* * * * *